United States Patent
LaVoie et al.

(10) Patent No.: US 10,556,854 B2
(45) Date of Patent: Feb. 11, 2020

(54) BACTERIAL EFFLUX PUMP INHIBITORS

(71) Applicant: RUTGERS, THE STATE UNIVERSITY OF NEW JERSEY, New Brunswick, NJ (US)

(72) Inventors: Edmond J. LaVoie, New Brunswick, NJ (US); Gifty A. Blankson, New Brunswick, NJ (US); Ajit Parhi, New Brunswick, NJ (US); Malvika Kaul, New Brunswick, NJ (US); Daniel S. Pilch, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/078,576

(22) PCT Filed: Feb. 23, 2017

(86) PCT No.: PCT/US2017/019194
§ 371 (c)(1),
(2) Date: Aug. 21, 2018

(87) PCT Pub. No.: WO2017/147333
PCT Pub. Date: Aug. 31, 2017

(65) Prior Publication Data
US 2019/0084919 A1    Mar. 21, 2019

Related U.S. Application Data

(60) Provisional application No. 62/299,434, filed on Feb. 24, 2016.

(51) Int. Cl.
| | |
|---|---|
| *C07C 211/27* | (2006.01) |
| *A61K 45/06* | (2006.01) |
| *A61K 31/137* | (2006.01) |
| *A61K 31/138* | (2006.01) |
| *C07C 211/00* | (2006.01) |
| *C07C 217/42* | (2006.01) |
| *A61P 31/04* | (2006.01) |
| *A61K 9/00* | (2006.01) |
| *A61K 47/02* | (2006.01) |
| *A61K 9/20* | (2006.01) |
| *A61K 9/48* | (2006.01) |

(52) U.S. Cl.
CPC .......... *C07C 211/27* (2013.01); *A61K 31/137* (2013.01); *A61K 31/138* (2013.01); *A61K 45/06* (2013.01); *A61P 31/04* (2018.01); *C07C 211/00* (2013.01); *C07C 217/42* (2013.01); *A61K 9/0019* (2013.01); *A61K 9/0078* (2013.01); *A61K 9/2018* (2013.01); *A61K 9/2054* (2013.01); *A61K 9/4858* (2013.01); *A61K 47/02* (2013.01); *Y02A 50/401* (2018.01); *Y02A 50/475* (2018.01)

(58) Field of Classification Search
CPC .............................. C07C 211/27; A61P 31/04
See application file for complete search history.

(56) References Cited

U.S. PATENT DOCUMENTS

| | | | |
|---|---|---|---|
| 6,204,279 B1 | 3/2001 | Leger et al. | |
| 9,926,261 B2 | 3/2018 | LaVoie et al. | |
| 9,950,993 B2 | 4/2018 | LaVoie et al. | |
| 2019/0031624 A1 | 1/2019 | LaVoie et al. | |

FOREIGN PATENT DOCUMENTS

| | | |
|---|---|---|
| WO | 2018165611 A1 | 9/2018 |
| WO | 2018165612 A1 | 9/2018 |
| WO | 2018165614 A1 | 9/2018 |
| WO | 2018218192 A1 | 11/2018 |
| WO | 2019005841 A1 | 1/2019 |

OTHER PUBLICATIONS

Patent Cooperation Treaty, International Searching Authority, Search Report and Written Opinion for PCT/US2017/019194, 10 pages, dated Jun. 20, 2017.
Pubchem, "10143777", CID 101437777, 9 pages, Create Date Dec. 18, 2015.
Pubchem, "10954401", CID 10954401, 14 pages, Create Date Oct. 26, 2006.
Pubchem, "67894517", CID 67894517, 10 pages, Create Date Nov. 30, 2012.

*Primary Examiner* — Golam M Shameem

(74) *Attorney, Agent, or Firm* — Viksnins Harris Padys Malen LLP

(57) ABSTRACT

Disclosed herein are compounds of formula I: and salts thereof. Also disclosed are compositions comprising compounds of formula I and methods using compounds of formula I.

(I)

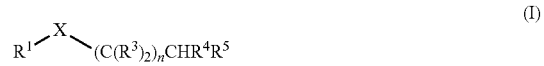

20 Claims, No Drawings

BACTERIAL EFFLUX PUMP INHIBITORS

PRIORITY OF INVENTION

This application claims priority from U.S. Provisional Patent Application No. 62/299,434 filed Feb. 24, 2016, which is hereby incorporated by reference in its entirety.

BACKGROUND OF THE INVENTION

Antibiotics have been effective tools in the treatment of infectious diseases. However, bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with a known antibiotic, lower the minimum inhibitory concentration of the known antibiotic to inhibit bacterial cell growth.

Not to be bound by theory the compounds are believed to exert this effect by the inhibition of a bacterial efflux pump(s).

Accordingly, one embodiment provides a compound of formula I:

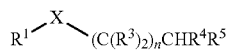

X is $NR^2$ or O;
$R^1$ is $(C_3-C_{12})$alkyl substituted with two or more groups selected from $-NR^{b1}R^{c1}$, $-NHNH_2$, $-C(=NR^{a1})(NR^{b1}R^{c1})$, $-NR^{a1}C(=NR^{a1})(R^{d1})$ and $-NR^{a1}C(=NR^{a1})(NR^{b1}R^{c1})$;

$R^2$ is hydrogen or $(C_1-C_3)$alkyl;
each $R^3$ is independently hydrogen, halo or $(C_1-C_4)$alkyl;
$R^4$ is aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^5$ is hydrogen, $(C_1-C_3)$alkyl, aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy, provided that when $R^5$ is hydrogen or $(C_1-C_3)$alkyl, and $R^4$ is optionally substituted phenyl, then n is not 0 or 1;
each $R^{a1}$ is independently hydrogen or $(C_1-C_4)$alkyl;
each $R^{b1}$ and $R^{c1}$ is independently hydrogen or $(C_1-C_4)$alkyl;
$R^{d1}$ is $(C_1-C_3)$alkyl and
n is 0, 1, 2 or 3;
or a salt thereof.

One embodiment provides a compound of formula I:

X is $NR^2$ or O;
$R^1$ is $(C_3-C_{12})$alkyl substituted with two or more groups selected from $-NR^{b1}R^{c1}$, $-NHNH_2$, $-C(=NR^{a1})(NR^{b1}R^{c1})$, $-NR^{a1}C(=NR^{a1})(R^{d1})$ and $-NR^{a1}C(=NR^{a1})(NR^{b1}R^{c1})$;
$R^2$ is hydrogen or $(C_1-C_3)$alkyl;
each $R^3$ is independently hydrogen, halo or $(C_1-C_4)$alkyl;
$R^4$ is aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^5$ is hydrogen, $(C_1-C_3)$alkyl, aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy, provided that when $R^5$ is hydrogen or $(C_1-C_3)$alkyl, and $R^4$ is optionally substituted phenyl, then n is not 0;
each $R^{a1}$ is independently hydrogen or $(C_1-C_4)$alkyl;
each $R^{b1}$ and $R^{c1}$ is independently hydrogen or $(C_1-C_4)$alkyl;
$R^{d1}$ is $(C_1-C_3)$alkyl and
n is 0, 1, 2 or 3;
or a salt thereof.

One embodiment provides a pharmaceutical composition comprising a compound of formula I or a pharmaceutically acceptable salt thereof as described herein, and a pharmaceutically acceptable vehicle.

One embodiment provides a pharmaceutical composition comprising a compound of formula I or a pharmaceutically acceptable salt thereof as described herein, one or more antibacterial agents and a pharmaceutically acceptable vehicle.

One embodiment provides a method of inhibiting a bacterial efflux pump in an animal (e.g., a mammal such as a human) comprising administering to the animal a compound of formula I or a pharmaceutically acceptable salt thereof as described herein.

One embodiment provides a method of inhibiting a bacterial efflux pump in an animal (e.g., a mammal such as a human) comprising administering to the animal in need thereof a compound of formula I or a pharmaceutically acceptable salt thereof as described herein.

One embodiment provides a method of treating or preventing a bacterial infection in an animal (e.g., a mammal such as a human) comprising co-administering to the animal a compound of formula I or a pharmaceutically acceptable salt thereof as described herein and one or more antibacterial agents.

One embodiment provides a method of treating or preventing a bacterial infection in an animal (e.g., a mammal such as a human) comprising co-administering to the animal in need thereof a compound of formula I or a pharmaceutically acceptable salt thereof as described herein and one or more antibacterial agents.

One embodiment provides a method of inhibiting a bacterial efflux pump in an animal (e.g., a mammal such as a human) with a bacterial infection comprising administering to the animal a compound of formula I or a pharmaceutically acceptable salt thereof as described herein.

One embodiment provides a method of treating or preventing a bacterial infection in an animal (e.g., a mammal such as a human) infected with bacteria comprising co-administering to the animal a compound of formula I or a pharmaceutically acceptable salt thereof as described herein and one or more antibacterial agents.

One embodiment provides a compound of formula I or a pharmaceutically acceptable salt thereof as described herein for use in medical treatment.

One embodiment provides a compound of formula I or a pharmaceutically acceptable salt thereof as described herein for the prophylactic or therapeutic inhibition of a bacterial efflux pump for the treatment of a bacterial infection.

One embodiment provides a compound of formula I or a pharmaceutically acceptable salt thereof as described herein which is used in combination with one or more antibacterial agents for the prophylactic or therapeutic treatment of a bacterial infection.

One embodiment provides the use of a compound of formula I or a pharmaceutically acceptable salt thereof as described herein for the preparation of a medicament for inhibiting a bacterial efflux pump.

One embodiment provides the use of a compound of formula I or a pharmaceutically acceptable salt thereof as described herein for the preparation of a medicament for treating a bacterial infection in an animal (e.g., a mammal such as a human).

One embodiment provides the use of a compound of formula I or a pharmaceutically acceptable salt thereof as described herein for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a\text{-}C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$haloalkyl".

The term cycloalkyl includes saturated and partially unsaturated carbocyclic ring systems. In one embodiment the cycloalkyl is a monocyclic carbocyclic ring. One such cycloalkyl is a "$(C_3-C_8)$cycloalkyl".

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; $(C_1-C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is to be understood that the embodiments provided below are for compounds of formula I and all sub-formulas thereof (e.g., formulas Ia, Ib, Ic, Id). It is to be understood the two or more embodiments may be combined.

One embodiment provides a compound formula I which is a compound of formula Ia.

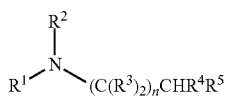

Ia or a salt thereof.

In one embodiment $R^2$ is hydrogen.

One embodiment provides a compound formula I which is a compound of formula Ib:

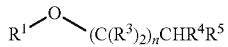

Ib or a salt thereof.

In one embodiment each $R^3$ is hydrogen.

One embodiment provides a compound formula I which is a compound of formula Ia.

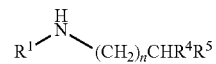

Ic or a salt thereof.

One embodiment provides a compound formula I which is a compound of formula Id.

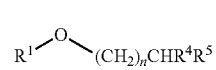

Id or a salt thereof.

In one embodiment n is 0, 1 or 2.

In one embodiment n is 0 or 1.

In one embodiment $R^4$ is aryl or aryl$(C_1-C_6)$alkyl- wherein any aryl or aryl$(C_1-C_6)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^4$ is phenyl or phenyl$(C_1-C_3)$alkyl- wherein any phenyl or phenyl$(C_1-C_3)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^4$ is phenyl$(C_1-C_3)$alkyl- wherein any phenyl$(C_1-C_3)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^4$ is:

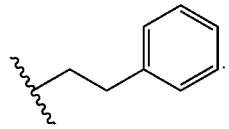

In one embodiment $R^5$ is hydrogen, aryl or aryl$(C_1-C_6)$alkyl- wherein any aryl or aryl$(C_1-C_6)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy, provided that when $R^5$ is hydrogen and $R^4$ is optionally substituted phenyl, then n is not 0.

In one embodiment $R^5$ is hydrogen, phenyl or phenyl$(C_1-C_6)$alkyl- wherein any phenyl or phenyl$(C_1-C_6)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy provided that when $R^5$ is hydrogen and $R^4$ is optionally substituted phenyl, then n is not 0.

In one embodiment $R^5$ is hydrogen, phenyl or phenyl$(C_1-C_2)$alkyl- wherein any phenyl or phenyl$(C_1-C_2)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy provided that when $R^5$ is hydrogen and $R^4$ is optionally substituted phenyl, then n is not 0.

In one embodiment R⁵ is hydrogen, aryl or aryl(C₁-C₆)alkyl- wherein any aryl or aryl(C₁-C₆)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy, provided that when R⁵ is hydrogen and R⁴ is optionally substituted phenyl, then n is not 0 or 1.

In one embodiment R⁵ is hydrogen, phenyl or phenyl(C₁-C₆)alkyl- wherein any phenyl or phenyl(C₁-C₆)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy provided that when R⁵ is hydrogen and R⁴ is optionally substituted phenyl, then n is not 0 or 1.

In one embodiment R⁵ is hydrogen, phenyl or phenyl(C₁-C₂)alkyl- wherein any phenyl or phenyl(C₁-C₂)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy provided that when R⁵ is hydrogen and R⁴ is optionally substituted phenyl, then n is not 0 or 1.

In one embodiment R⁵ is aryl or aryl(C₁-C₆)alkyl- wherein any aryl or aryl(C₁-C₆)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁵ is phenyl or phenyl(C₁-C₆)alkyl- wherein any phenyl or phenyl(C₁-C₆)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁵ is phenyl or phenyl(C₁-C₂)alkyl- wherein any phenyl or phenyl(C₁-C₂)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁵ is phenyl(C₁-C₂)alkyl- wherein any phenyl(C₁-C₂)alkyl- of R⁵ is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁵ is hydrogen,

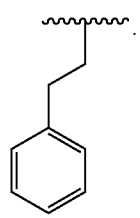

In one embodiment the moiety —(C(R³)₂)ₙCHR⁴R⁵ of the compound of formula I is:

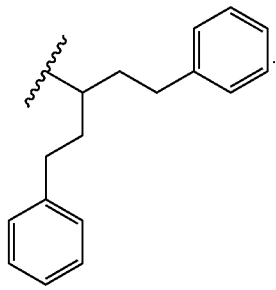 [SMILES: *C(CCc1ccccc1)CCc1ccccc1]

In one embodiment the moiety —(C(R³)₂)ₙCHR⁴R⁵ of the compound of formula I is:

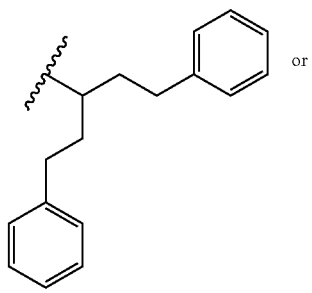 or

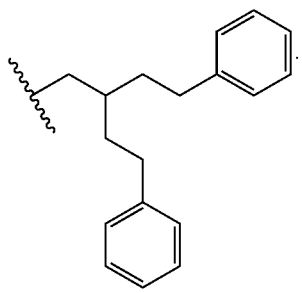

In one embodiment R¹ is (C₃-C₁₂)alkyl substituted with two or more groups independently selected from —NR^{b1}R^{c1}.

In one embodiment R¹ is (C₃-C₁₂)alkyl substituted with two groups independently selected from —NR^{b1}R^{c1}.

In one embodiment R¹ is (C₄-C₈)alkyl substituted with two groups independently selected from —NR^{b1}R^{c1}.

In one embodiment R^{b1} and R^{c1} are each hydrogen.

In one embodiment R¹ is

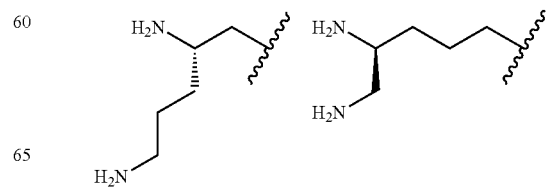

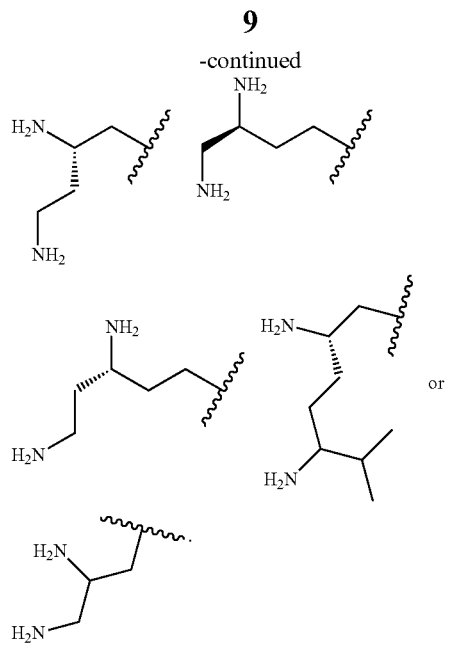
One embodiment provides a compound of formula I which is:
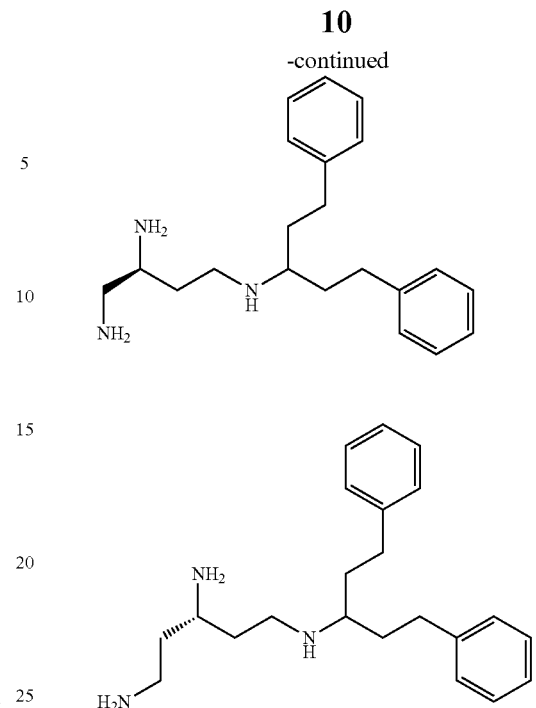
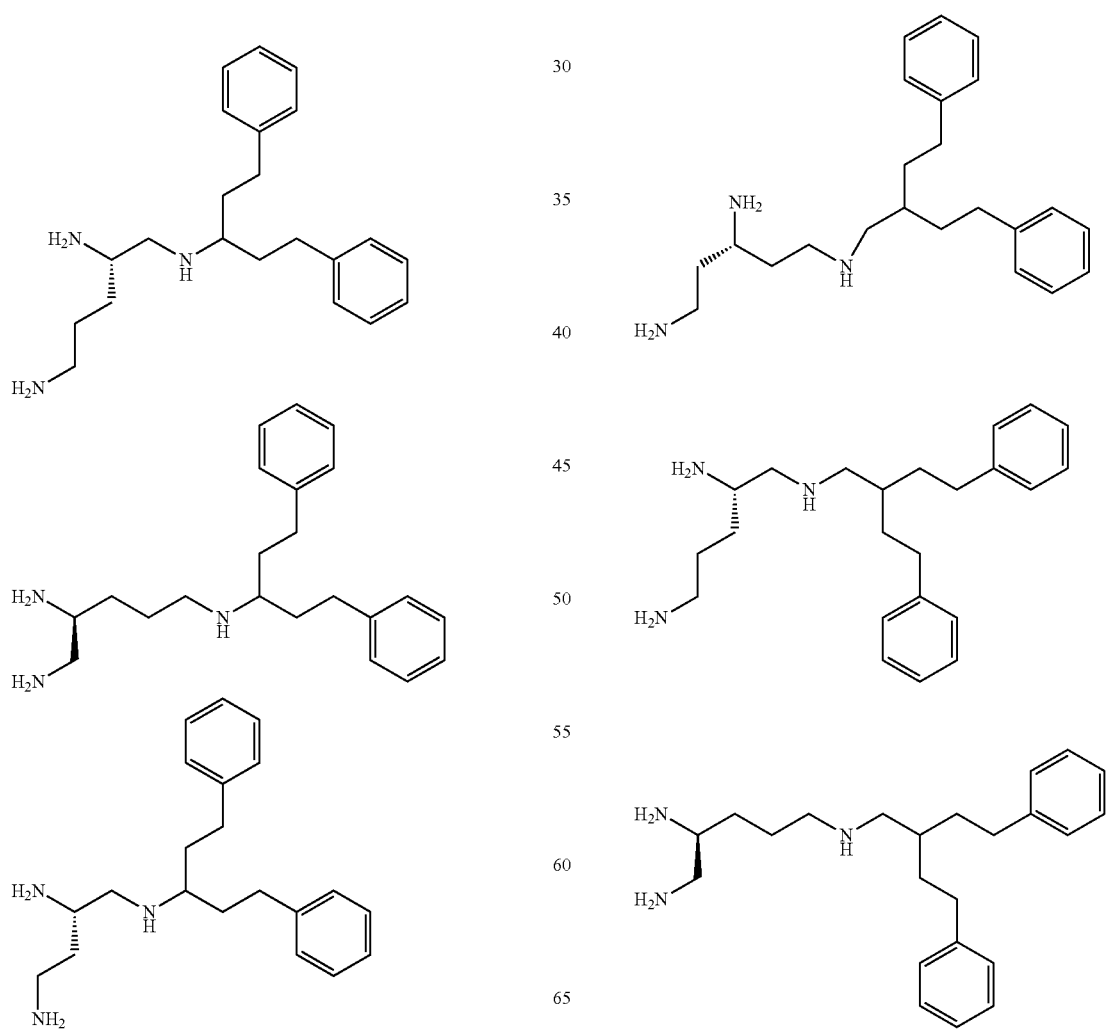

-continued
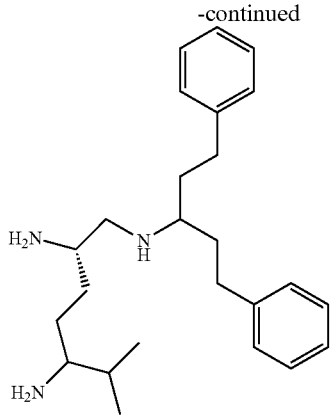
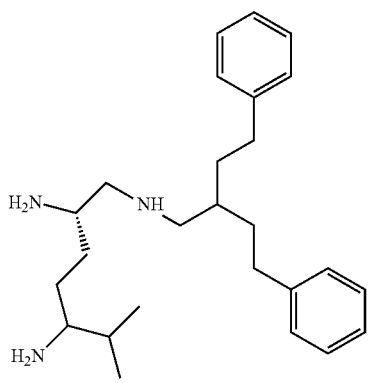
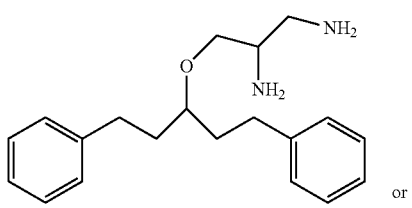
or
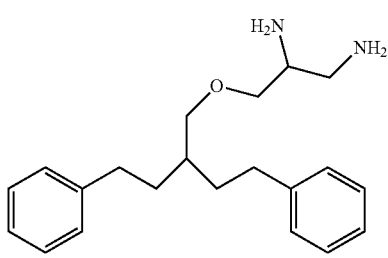
or a salt thereof.
One embodiment provides a compound of formula I which is:
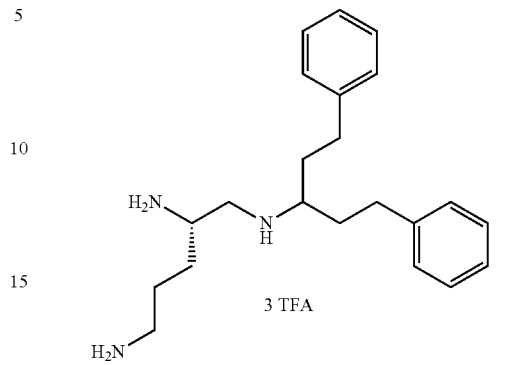
3 TFA
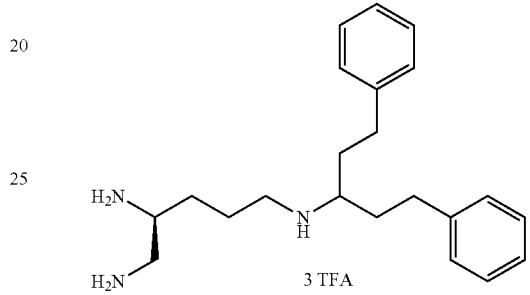
3 TFA
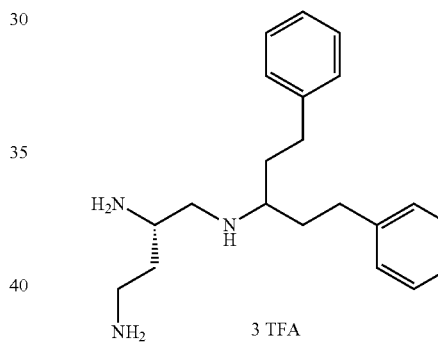
3 TFA
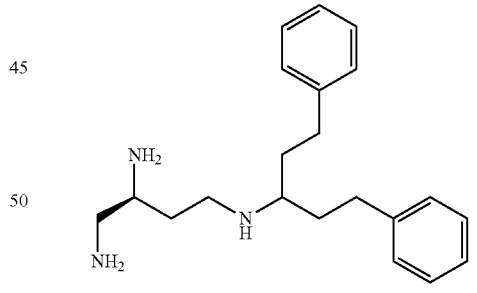
3 TFA
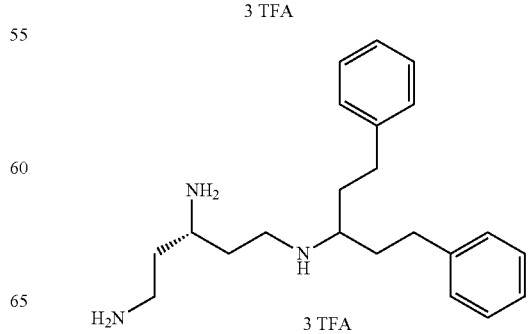
3 TFA

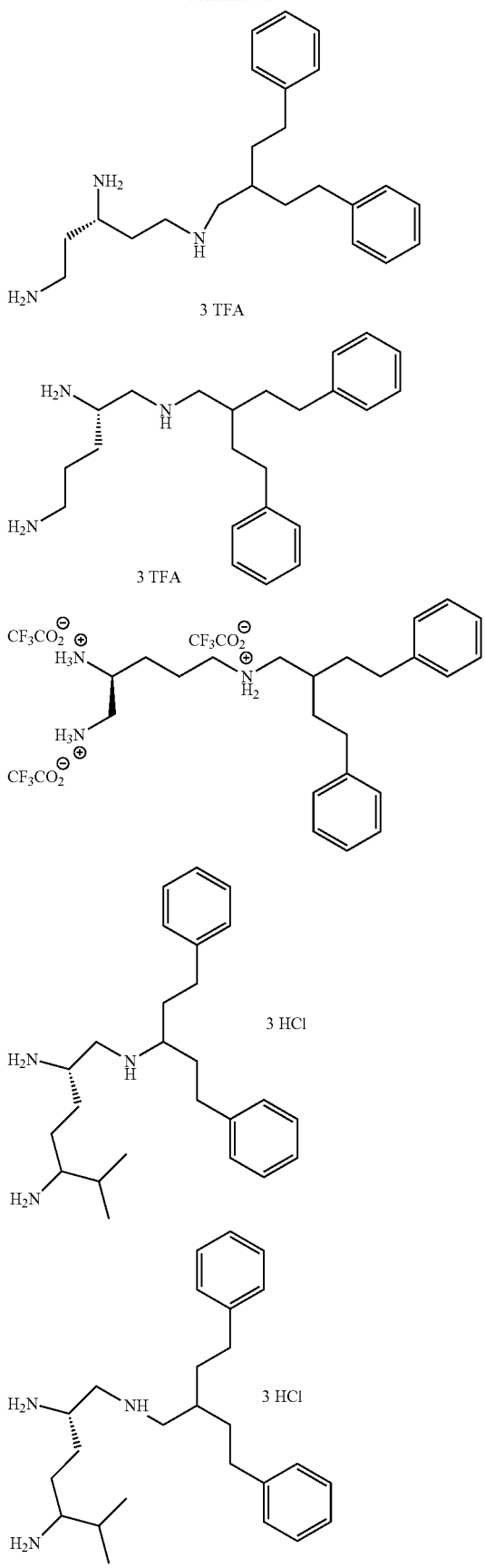

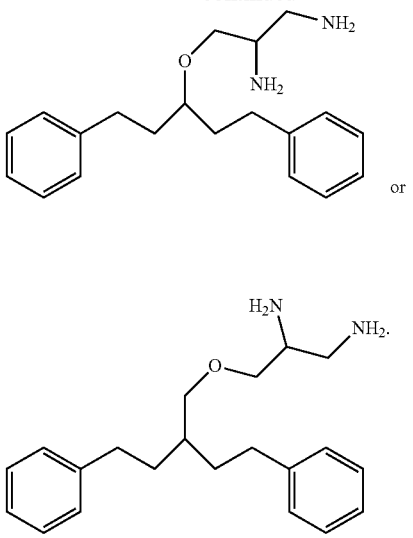

Generally, compounds of formula I as well as synthetic intermediates that can be used for preparing compounds of formula I can be prepared as illustrated in the following General Methods and Schemes. It is understood that variable groups shown below (e.g., w, n, m, p, R X and Y) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I. Methods that can be employed for the preparation of compounds of formula I are provided, but are not limited, to those illustrated in the following general synthetic schemes (Schemes 1-9). It is to be understood that for the methods of Scheme 1-9 the phenyl can be replaced with a heteroaryl). The variable Pg is a protecting group and such as an amine protecting group. Amine protecting groups are well known in the art and any suitable amine protecting group may be used (e.g., acetyl, trifluoroacetyl, benzyl, triphenylmethyl, benzylidenyl, p-toluenesulfonyl, p-methoxybenzyl, tert-butyloxycarbonyl, 9-fluorenylmethyloxycarbonyl and carbobenzyloxy).

Scheme 1.

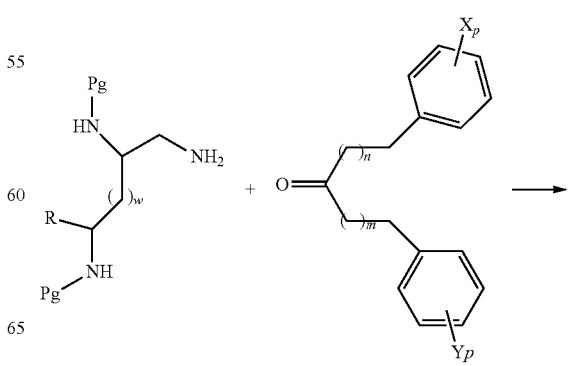

15
-continued

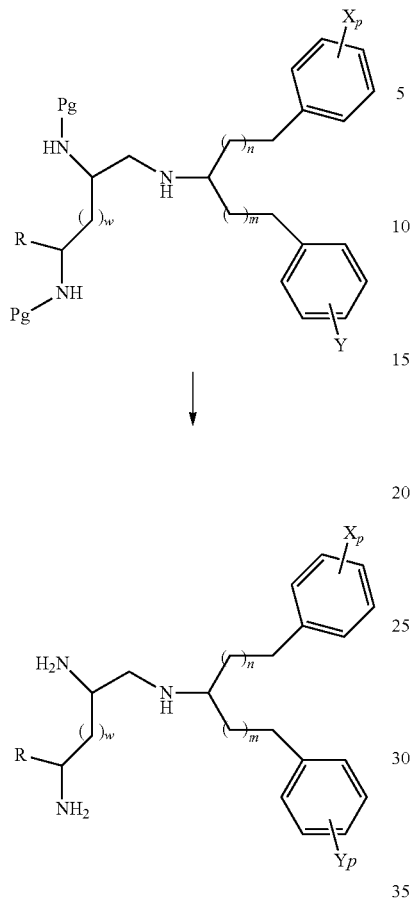

Wherein w=0-4; n=0-2; m=0-2; p=0-5; R=H or an alkyl substituent; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy) and Pg is a protecting group (e.g., an amine protecting group).

Reductive amination with the appropriately protected diamine derivative will provide the desired secondary (or tertiary amine) that can be deprotected to yield the triaminoalkylaryl derivative.

16
-continued

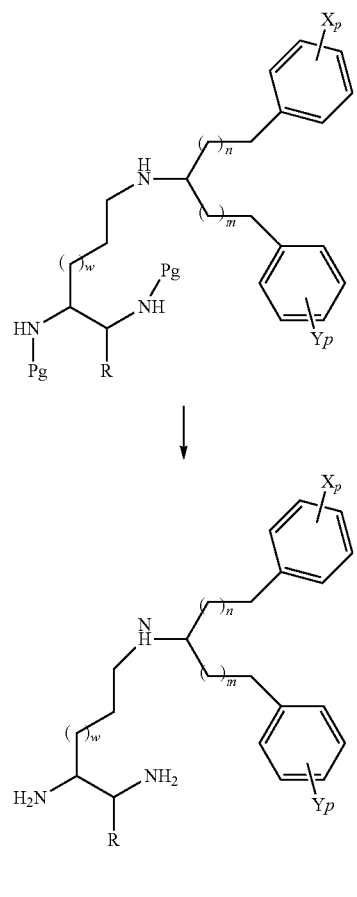

Wherein w=0-4; n=0-2; m=0-2; p=0-5; R=H or an alkyl substituent; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy) and Pg is a protecting group (e.g., an amine protecting group).

In a similar manner as shown in Scheme 1, a diprotected alkyltriamine can be coupled by reductive amination with the appropriately substituted alkylaryl ketone to provide the desired secondary (or tertiary amine) that can be deprotected to yield the triaminoalkylaryl derivative. The difference is the relative position of the N-protected amino substituted on the triaminoalkane.

Scheme 2.

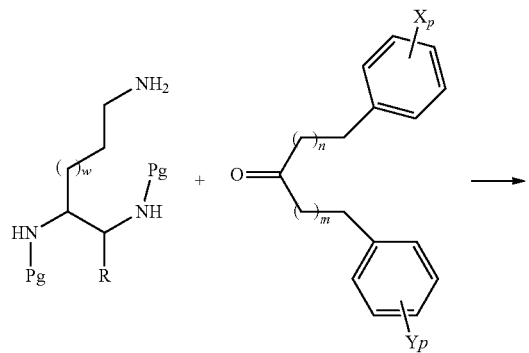

Scheme 3.

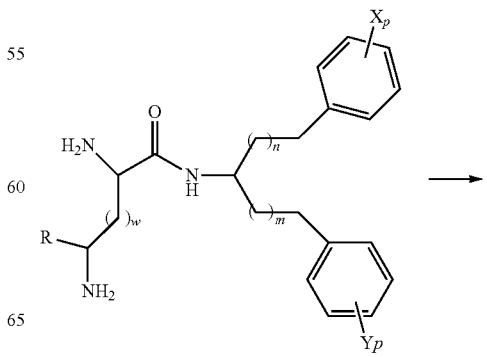

-continued

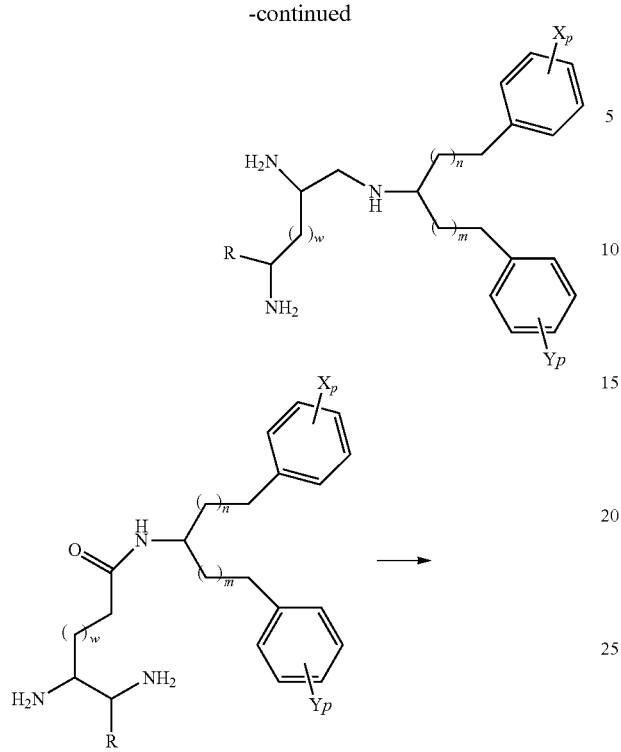

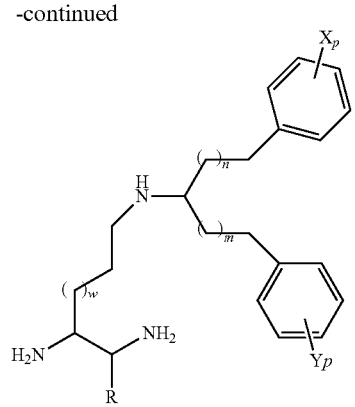

Wherein w=0-4; n=0-2; m=0-2; p=0-5; R=H or an alkyl substituent; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy).

Reduction of the amide substituent of the appropriately substituted alkylaryl amide to its secondary (or tertiary) amine provides an alternative approach for the formation of compounds of Formula 1 as illustrated for the two varied substituted amides shown in Scheme 3.

Scheme 4.

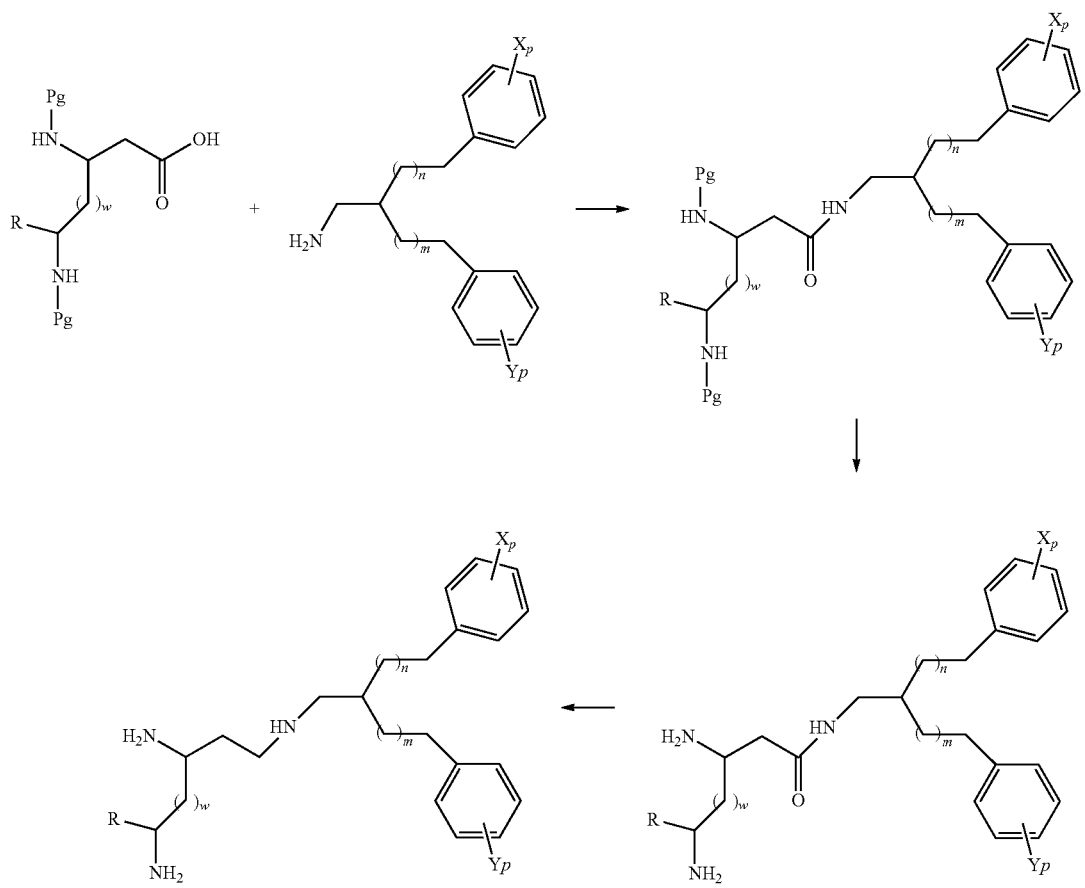

Wherein w=0-4; n=0-2; m=0-2; p=0-5; R=H or an alkyl substituent; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy).

Scheme 4 illustrates the coupling of a primary amine (or secondary amine) on the alkylaryl moiety with an appropriately substituted diamino acid. As indicated in this scheme, the amines have modified with a protecting group, which can be removed prior to or after conversion of the resulting amide to a secondary (or tertiary) amine derivative.

Scheme 5.

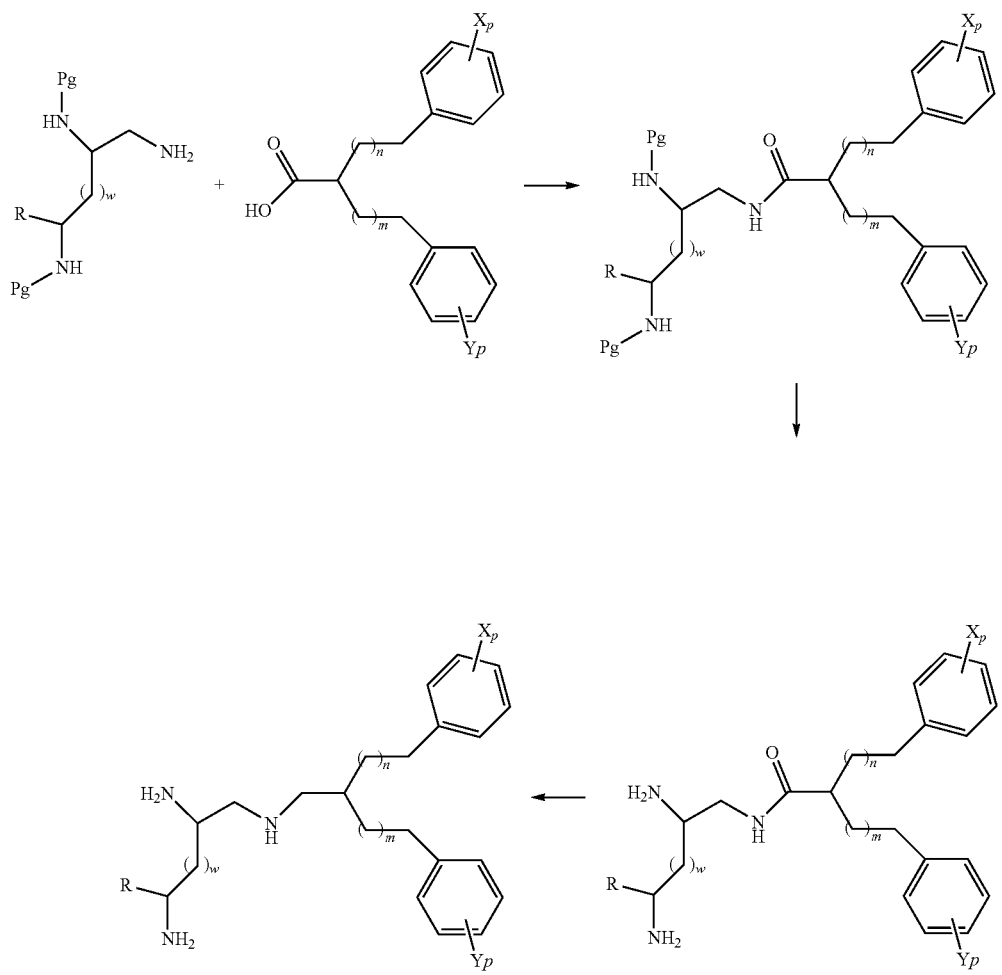

Wherein w=0-4; n=0-2; m=0-2; p=0-5; R=H or an alkyl substituent; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy) and Pg is a protecting group (e.g., an amine protecting group).

Scheme 6

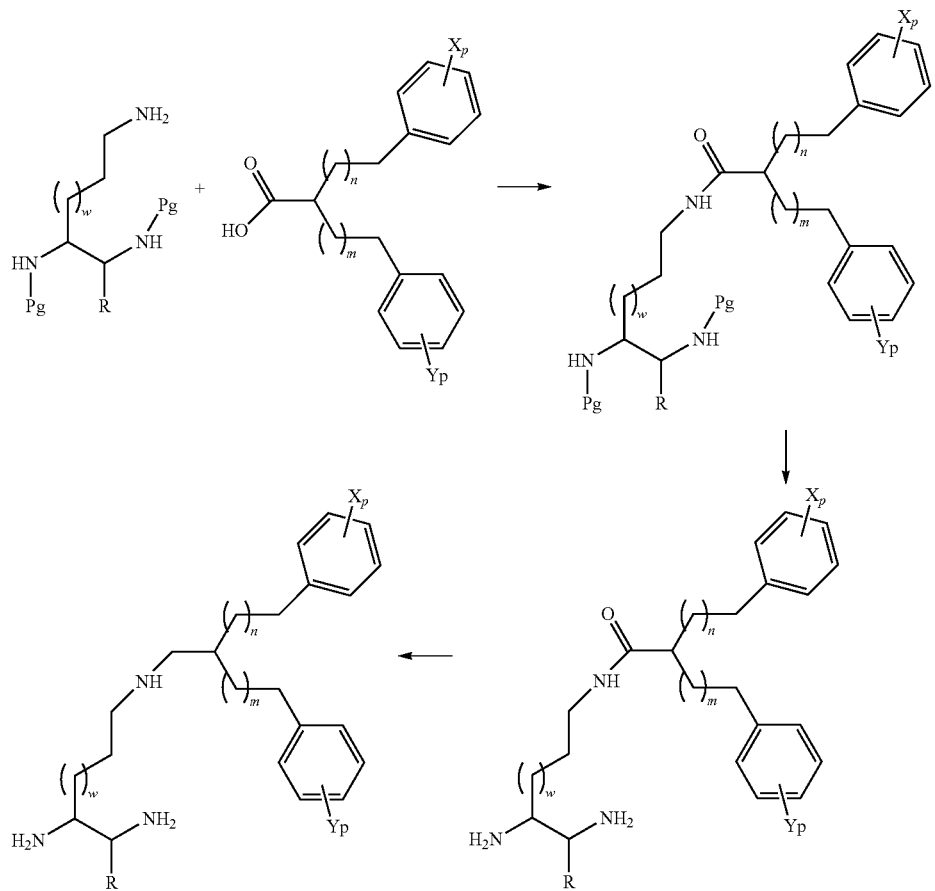

Wherein w=0-4; n=0-2; m=0-2; p=0-5; R=H or an alkyl substituent; and X and Y are each independently H or a substituent (e.g., halo, $(C_1\text{-}C_4)$alkyl, $(C_1\text{-}C_4)$haloalkyl, $(C_1\text{-}C_4)$alkoxy and $(C_1\text{-}C_4)$haloalkoxy) and Pg is a protecting group (e.g., an amine protecting group).

Schemes 5 and 6 illustrate the varied derivatives that can be formed using by coupling the carboxylic acid of the alkylaryl moiety with a diprotected triaminoalkyl derivative. Coupling to form the amide followed by deprotection of the amine functionalities and reduction of the amide to either its secondary or tertiary amine would provide additional compounds of formula 1.

Scheme 7

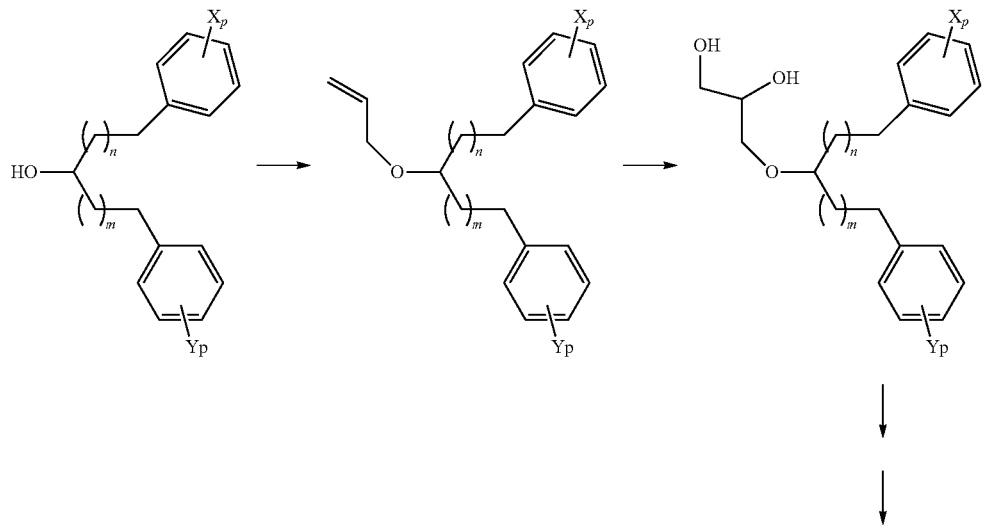

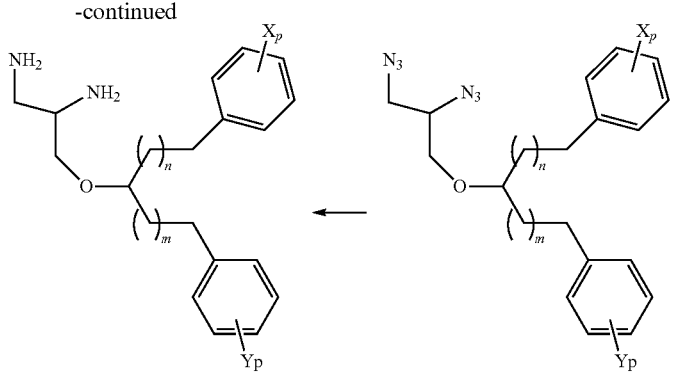

Wherein n=0-2; m=0-2; p=0-5; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy).

Using a secondary alcohol substituent on the alkylaryl derivative provides a means for formation of the desired diaminoether derivatives of formula 1. Formation of an ally ether, for example, followed by oxidation of the olefin to its diol allows for the formation of a dimesylate derivative that can be converted to the di azide. Reduction of the di azide will provide the diamino ether.

Scheme 8

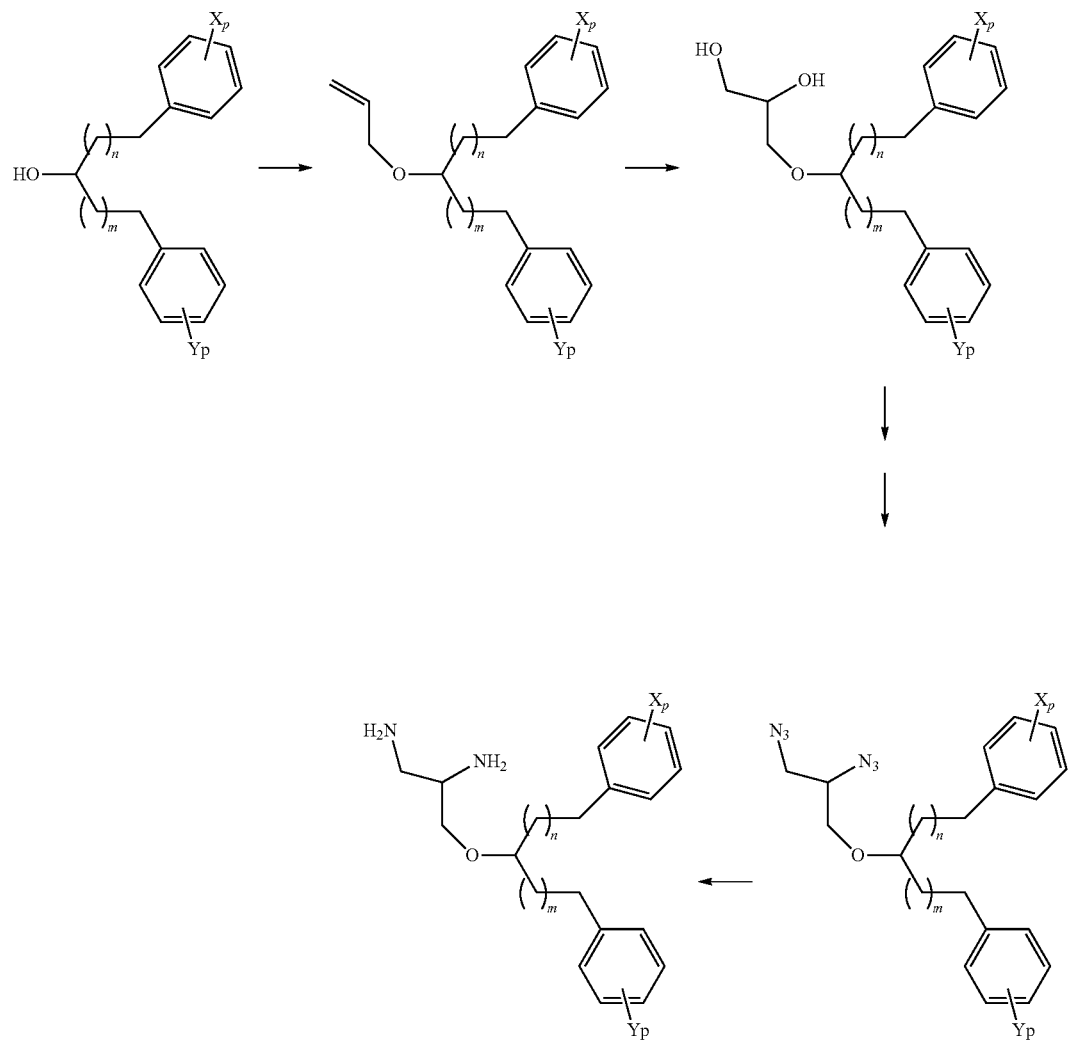

Wherein n=0-2; m=0-2; p=0-5; and X and Y are each independently H or a substituent (e.g., halo, $(C_1-C_4)$alkyl, $(C_1-C_4)$haloalkyl, $(C_1-C_4)$alkoxy and $(C_1-C_4)$haloalkoxy). Scheme 8 illustrated how a primary hydroxyl moiety on the alkylaryl derivative can also serve as a useful intermediate for the formation of diamino ether of Formula 1.

The compounds disclosed herein are bacterial efflux pump inhibitors. An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophila, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella flexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis.*

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin, a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, rifamycins, macrolides, ketolides, oxazolidinones, coumermycins, and chloramphenicol.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method like Test A or Test B as described in Example 13 and as shown in Table 1.

TABLE 1

| Example | STRUCTURE | Active in E. coli | Active in P. aeruginosa |
|---|---|---|---|
| 1 | 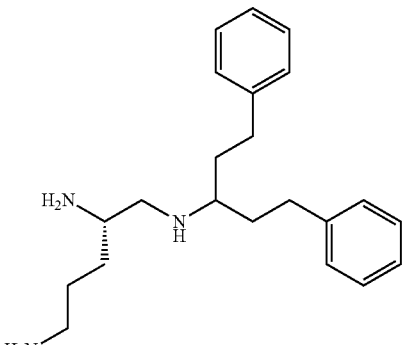 3 TFA | ≥8x | <2x |
| 2 | 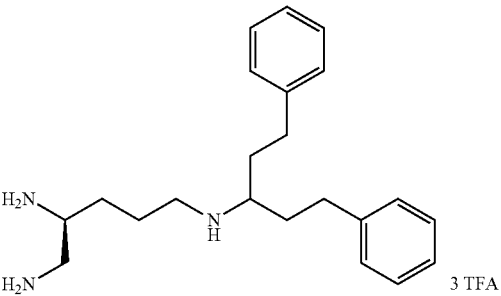 [SMILES: NC[C@@H](N)CCCNC(CCc1ccccc1)CCc1ccccc1] 3 TFA | ≥16x | ≥4x |

TABLE 1-continued
| Example | STRUCTURE | Active in E. coli | Active in P. aeruginosa |
|---|---|---|---|
| 3 | 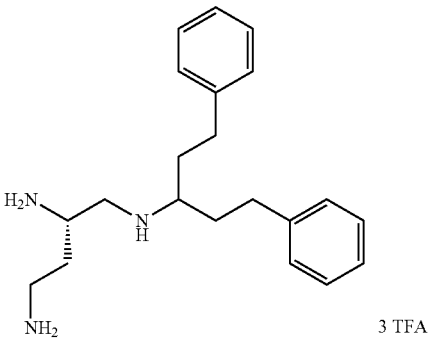 [SMILES: NCC[C@H](N)CNC(CCc1ccccc1)CCc1ccccc1] 3 TFA | ≥4x | ≥2x |
| 4 | 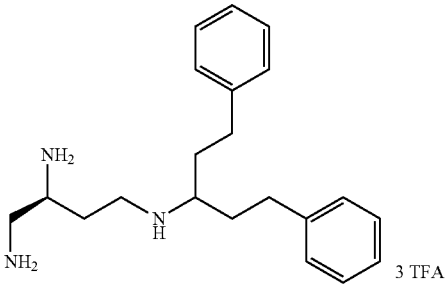 [SMILES: NC[C@@H](N)CCNC(CCc1ccccc1)CCc1ccccc1] 3 TFA | ≥2x | ≥2x |
| 5 | 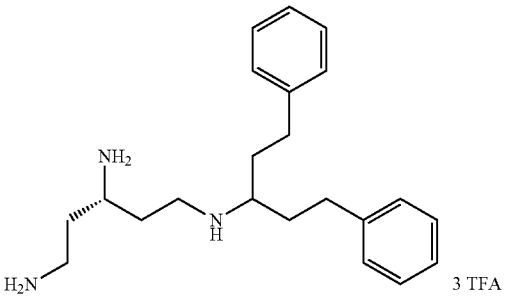 [SMILES: NCC[C@H](N)CCNC(CCc1ccccc1)CCc1ccccc1] 3 TFA | ≥32x | ≥16x |
| 6 | 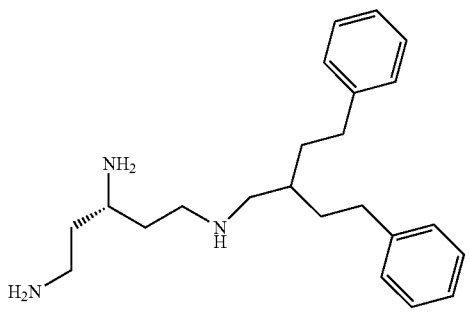 3 TFA | ND | ND |
| 7 | 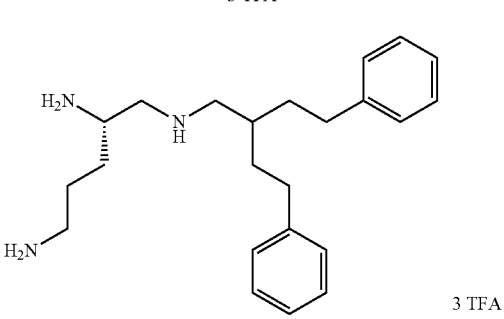 3 TFA | ≥32x | ≥32x |

TABLE 1-continued
| Example | STRUCTURE | Active in E. coli | Active in P. aeruginosa |
|---------|-----------|-------------------|--------------------------|
| 8 | 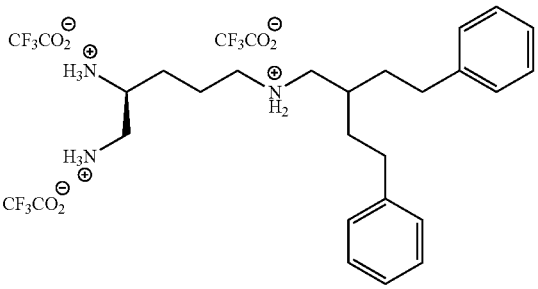 [SMILES: "CF3CO2" ; "CF3CO2" ; [NH3+]C[C@@H]([NH3+])CCC[NH2+]CC(CCc1ccccc1)CCc1ccccc1 ; "CF3CO2"] | ≥32x | ≥32x |
| 9 | 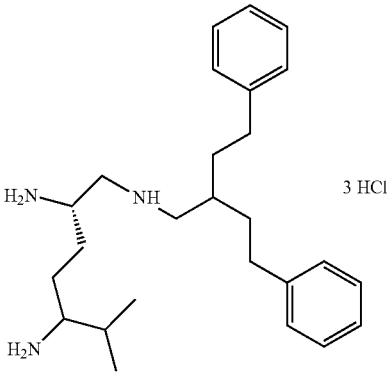 [SMILES: CC(C)C(N)CC[C@H](N)CNCC(CCc1ccccc1)CCc1ccccc1] 3 HCl | ≥128x | <2x |
| 10 | 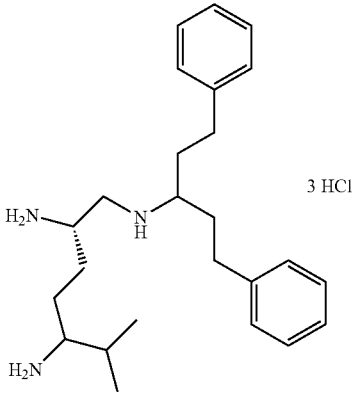 [SMILES: CC(C)C(N)CC[C@H](N)CNC(CCc1ccccc1)CCc1ccccc1] 3 HCl | ≥256 | <2x |
| 11 | 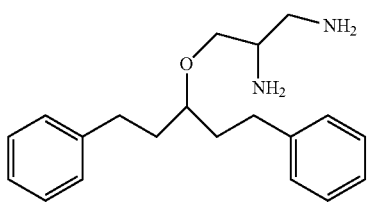 [SMILES: NCC(N)COC(CCc1ccccc1)CCc1ccccc1] | <2x | <2x |
| 12 | 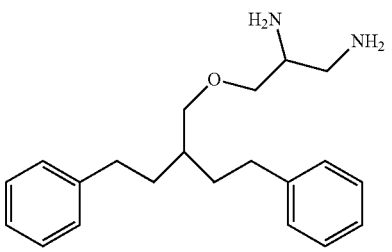 [SMILES: NCC(N)COCC(CCc1ccccc1)CCc1ccccc1] | 8 | <2x |

The invention will now be illustrated by the following non-limiting examples.

Example 1. Preparation of (S)—N1-(1,5-diphenyl-pentan-3-yl)pentane-1,2,5-triamine 3 TFA

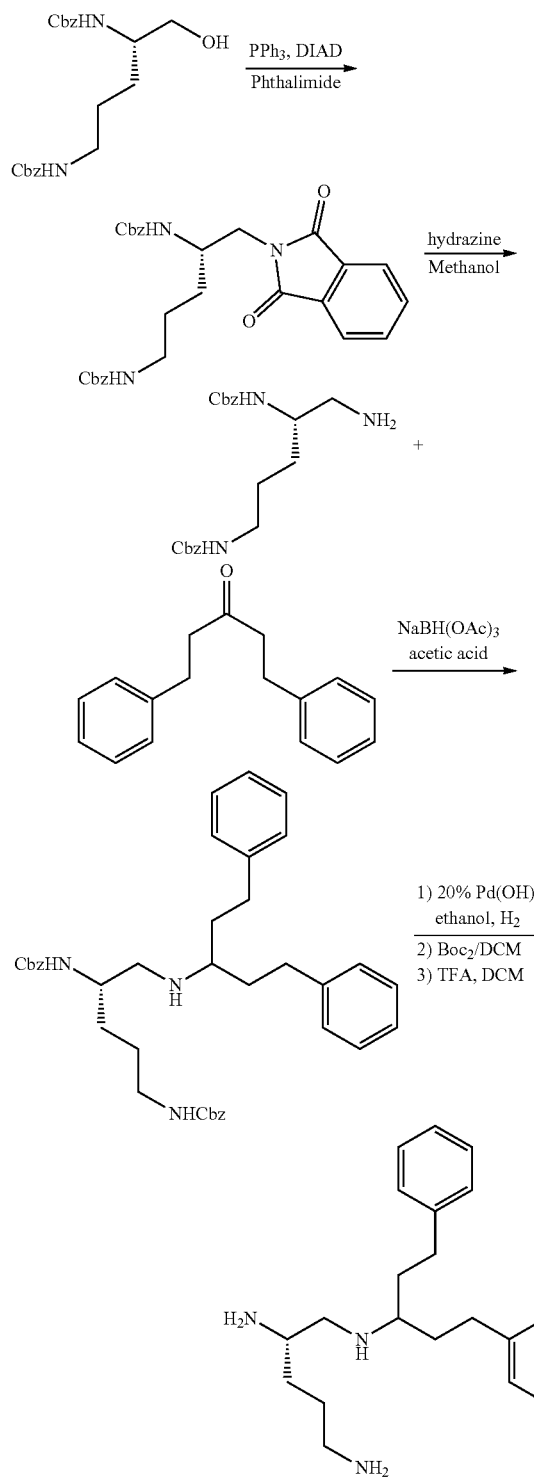

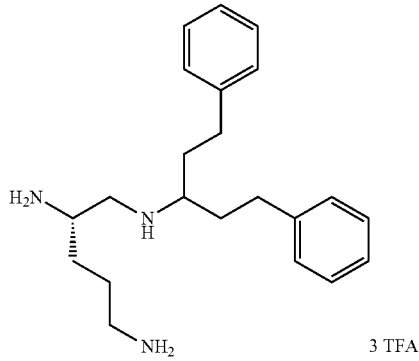 [SMILES: NCCC[C@H](N)CNC(CCc1ccccc1)CCc1ccccc1]

(S)—N¹-(1,5-Diphenylpentan-3-yl)pentane-1,2,5-triamine 3 TFA

A solution of dibenzyl (5-((1,5-diphenylpentan-3-yl)amino)pentane-1,4-diyl)(S)-dicarbamate (116 mg, 0.19 mmol) in ethanol (10 mL) was treated with 20% Pd(OH)$_2$/C (40 mg) and the mixture was purged. The solution was then stirred under hydrogen gas overnight. The catalyst was then filtered and washed with ethanol, which was rotavapped to give the crude product. The crude product was dissolved in 5 mL of dichloromethane and Boc$_2$O was added. The reaction mixture was stirred at room temperature for 1 hour and solvent removed. The residue was purified to give the boc-protected product, which was stirred with TFA (0.5 mL) and DCM (1 mL) for 1 hour to give product as the TFA salt. (colorless oil, 21 mg, 17%); $^1$H NMR (MeOD) (400 MHz) δ 7.15 (m, 10H), 3.61 (m, 1H), 3.27 (m, 3H), 2.87 (m, 2H), 2.65 (m, 4H), 2.02 (m, 4H), 1.73 (m, 4H); $^{13}$C NMR (MeOD) (100 MHz) δ 141.6, 129.7, 129.4, 127.4, 60.6, 39.9, 32.9, 32.7, 31.9, 29.3, 24.2.

The requisite intermediates were prepared as described in the following paragraphs.

Intermediate a

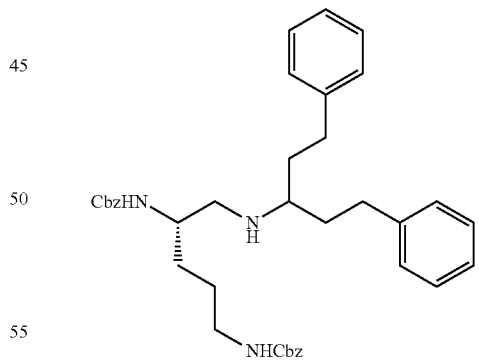

Dibenzyl (5-((1,5-diphenylpentan-3-yl)amino)pentane-1,4-diyl)(S)-dicarbamate

To a solution of 1,5-diphenylpentan-3-one (84 mg, 0.35 mmol), acetic acid (0.1 mL, 1.77 mmol) and dibenzyl (5-aminopentane-1,4-diyl)(S)-dicarbamate (150 mg, 0.39 mmol) in Methanol (5 mL) was added portionwise NaCNBH$_3$ (24.4 mg, 0.39 mmol). The reaction was stirred at room temperature for 17 hrs and concentrated in vacuo.

The residue was partitioned between aqueous K₂CO₃ and DCM. The organic layer was separated and dried over sodium sulfate and solvent evaporated and purified on ISCO (10% MeOH/DCM+1% NH₄OH) to give product as a white solid. (123.3 mg, 57%); mp 75-76 OC; 1H NMR (CDCl₃) (400 MHz) δ 7.83 (m, 2H), 7.28 (m, 20H), 5.13 (m, 6H), 3.67 (m, 1H), 3.22 (m, 2H), 2.54 (m, 7H), 1.62 (m, 9H); 13 C δ 156.5, 156.4, 142.3, 142.2, 136.7, 136.6, 128.5, 128.44, 128.42, 128.37, 128.35, 128.0, 125.9, 125.8, 66.6, 56.7, 51.0, 49.8, 40.8, 35.9, 35.6, 32.1, 30.4, 26.5

Intermediate b

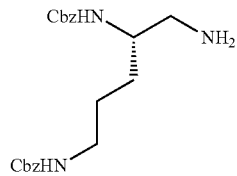 [SMILES: NC[C@H](CCCNC(=O)OCc1ccccc1)NC(=O)OCc1ccccc1]

Dibenzyl (5-aminopentane-1,4-diyl)(S)-dicarbamate

The phthalimide (400 mg, 0.78 mmol) formed was dissolved in methanol (20 mL) and hydrazine monohydrate (0.08 mL, 1.55 mmol) was added. The reaction mixture was then refluxed for 2 hrs and cooled to room temperature. The precipitate formed was filtered and methanol used to wash the filtrate. The filtrate was rotavapped and the remaining solid purified on ISCO (0-10% Methanol/DCM+1% NH₄OH) to give product as a white powder. (206 mg, 68%)%); mp 104-105° C.; 1H NMR (CDCl₃) (400 MHz) δ 7.36 (m, 10H), 5.18 (m, 6H), 3.60 (m, 1H), 3.19 (m, 2H), 2.70 (m, 2H), 1.70 (s 2H), 1.46 (m, 4H); ¹³C δ 156.6, 136.6, 136.5, 128.53, 128.51, 128.1, 128.0, 66.6, 66.5, 53.0, 45.6, 40.7, 29.7, 26.5

Intermediate c

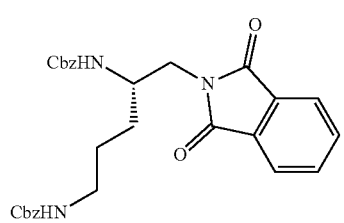 [SMILES: O=C(NCCC[C@@H](CN1C(=O)c2ccccc2C1=O)NC(=O)OCc1ccccc1)OCc1ccccc1]

Dibenzyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was rotavapped and residue purified on ISCO (0-70% Ethyl acetate/hexane) to give product as a white solid. (491 mg, 92%); mp 135-137° C.; 1H NMR (CDCl₃) (400 MHz) δ 7.83 (m, 2H), 7.72 (m, 2H), 7.32 (m, 10H), 5.10 (m, 3H), 4.97 (m, 3H), 4.03 (m, 1H) 3.76 (m, 2H), 3.24 (m, 2H), 1.57 (m, 4H); 13 C δ 168.5, 156.4, 156.2, 136.6, 136.5, 134.0, 132.1, 123.0, 131.9, 131.8, 128.6, 128.5, 128.4, 128.3, 128.0, 127.9, 127.8, 123.4, 66.6, 66.5, 50.7, 41.7, 40.6, 30.0, 26.3

Intermediate d

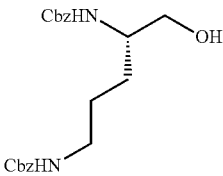 [SMILES: O=C(NCCC[C@@H](CO)NC(=O)OCc1ccccc1)OCc1ccccc1]

Dibenzyl (5-hydroxypentane-1,4-diyl)(S)-dicarbamate

To a solution of methyl (S)-2,5-bis(((benzyloxy)carbonyl)amino)pentanoate (1500 mg, 3.6 mmol) in THF/Ethanol(2:1) (15 mL) was added LiBH₄ (157 mg, 7.2 mmol) at 0° C. The mixture was stirred at that temperature for 30 minutes and warmed to room temperature and stirred for overnight. The reaction mixture was poured into water and extracted with ethyl acetate. The combine organic layers were washed with brine and dried over sodium sulfate and concentrated. It was purified on ISCO (0-70% ethyl acetate/hexane to give product as a white crystalline solid. (789 mg, 68%); mp 128-129° C.; 1H NMR (CDCl₃) (400 MHz) δ 7.35 (m, 10H), 5.11 (s, 4H), 5.00 (m, 2H), 3.65 (m, 3H), 3.22 (m, 2H), 1.54 (m, 4H); 13 C δ 156.6, 156.5, 136.5, 136.3, 128.54, 128.52, 128.2, 128.1, 66.8, 66.7, 65.1, 52.8, 40.7, 28.5, 26.5

Example 2. Preparation of (S)—N5-(1,5-diphenylpentan-3-yl)pentane-1,2,5-triamine 3 TFA

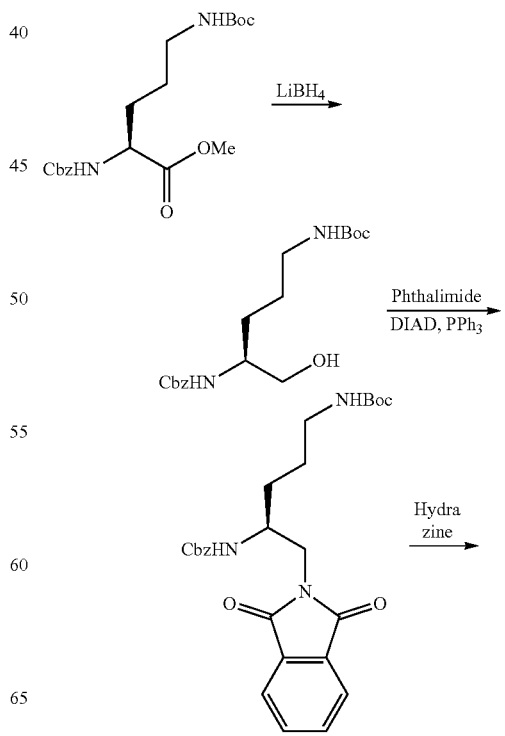

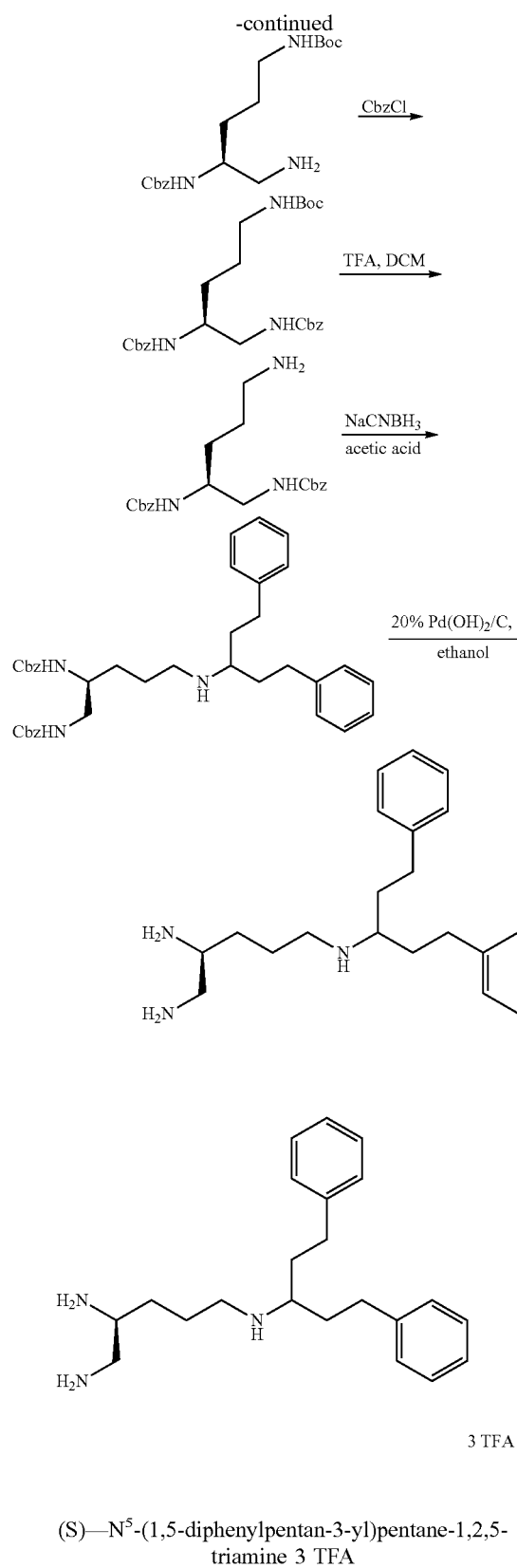

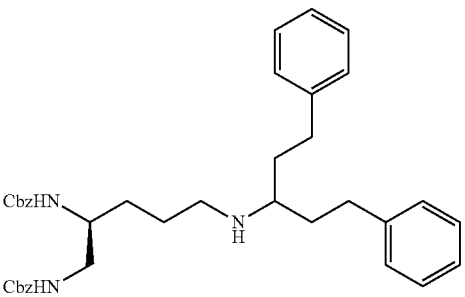 [SMILES: O=C(NC[C@H](CCCNC(CCc1ccccc1)CCc1ccccc1)NC(=O)OCc1ccccc1)OCc1ccccc1]

Dibenzyl (5-((1,5-diphenylpentan-3-yl)amino)pentane-1,2-diyl)(S)-dicarbamate

To a solution dibenzyl (5-aminopentane-1,2-diyl)(S)-dicarbamate (101.7 mg, 0.21 mmol), acetic acid and 1,5-diphenylpentan-3-one in Methanol was added portion wise NaBH$_3$CN. Reaction was stirred at room temperature for 17 h and concentrated in vacuo. The residue was partitioned between aqueous K$_2$CO$_3$ and DCM. The organic layer was separated and dried over anhydrous sodium sulfate and solvent evaporated in vacuo. The residue was purified on ISCO to give product as a white powder. (30 mg, 46% brsm); MP 82-84° C.; 1H NMR (CDCl3) (400 MHz) δ 7.16 (m, 20H), 5.42 (m, 1H), 5.20 (m, 1H), 4.99 (s, 2H), 4.98 (s, 2H), 3.61 (m, 1H), 3.20 (m, 2H), 2.52 (m, 6H), 1.68 (m, 4H), 1.44 (m, 5H); 13 C δ 142.3, 136.5, 128.5, 128.4, 128.3, 128.1, 128.5, 125.8, 66.8, 56.7, 51.7, 46.2, 45.3, 35.5, 32.0, 30.4, 26.4.

Intermediate b

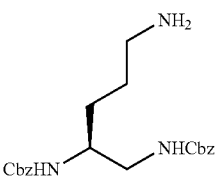 [SMILES: NCCC[C@@H](CNC(=O)OCc1ccccc1)NC(=O)OCc1ccccc1]

Dibenzyl (5-aminopentane-1,2-diyl)(S)-dicarbamate

Dibenzyl tert-butyl pentane-1,2,5-triyl(S)-tricarbamate (189 mg, 0.39 mmol) was dissolved in DCM (3 mL) and the reaction mixture cooled to 0° C. under Nitrogen. TFA (2 mL) was added and the reaction stirred at that temperature for 3 hrs. On completion of the reaction, the reaction was purged. It was then stirred overnight at room temperature under a hydrogen atmosphere. The catalyst was then filtered out by washing with 20% Methanol/DCM and the filtrate was concentrated and purified to give a colorless oil. The purified product was dissolved in DCM (1 mL) and TFA (0.5 mL) and stirred at room temperature for 2 hrs. On completion of the reaction, the solvents were removed and dried on a vacuum to give product (TFA salt) as a colorless oil. (6.0 mg, 100%); $^1$H NMR (MeOD) (400 MHz) δ 7.16 (M, 10H), 3.50 (M, 1 h), 3.16 (m, 4H), 2.96 (m, 2H), 2.64 (m, 4H), 1.98 (m, 4H), 1.73 (m, 4H); $^{13}$C δ 1.41.6, 129.7, 129.4, 127.5, 59.1, 50.2, 45.5, 41.9, 33.0, 32.0, 30.7, 28.8, 23.0

The requisite intermediates were prepared as described in the following paragraphs.

Intermediate a (S)—N$^5$-(1,5-diphenylpentan-3-yl)pentane-1,2,5-triamine 3 TFA

To a solution of dibenzyl (5-((1,5-diphenylpentan-3-yl)amino)pentane-1,2-diyl)(S)-dicarbamate (26 mg, 0.04 mmol) in ethanol (5 mL) was added 20% Pd(OH)$_2$/C (20 mg) and (BOC)$_2$O (23 mg, 0.11 mmol) and the mixture was quenched with saturated solution of NaHCO3 and extracted with DCM. The organic layer was rotavapped to give product as a yellow solid (101.7 mg, 67%); MP 85-87° C.; 1H NMR (CDCl3) (400 MHz) δ 7.17 (m, 10H), 5.51 (m, 1H), 4.90 (m, 4H), 3.54 (m, 4H), 3.05 (m, 2H), 2.84 (m, 2H), 1.43 (m, 4H); 13 C δ 161.3, 160.9, 160.5, 160.1, 158.0, 157.6, 135.7, 135.1, 128.6, 128.3, 127.7, 119.5, 116.6, 113.7, 68.3, 67.4, 51.2, 44.6, 39.9, 28.6, 23.4.

Intermediate c

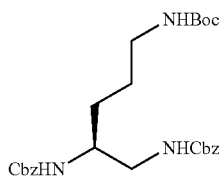 [SMILES: CC(C)(C)OC(=O)NCCC[C@@H](CNC(=O)OCc1ccccc1)NC(=O)OCc1ccccc1]

Dibenzyl tert-butyl pentane-1,2,5-triyl(S)-tricarbamate

Benzyl tert-butyl (5-aminopentane-1,4-diyl)(S)-dicarbamate (162.2 mg, 0.46 mmol) was dissolved in DCM (5 mL) under nitrogen atmosphere and triethylamine (0.08 mL, 0.55 mmol) was added. CbzCl (0.08 mL, 0.55 mmol) was added and reaction stirred at room temperature until the end of the reaction which was checked by TLC. The DCM was rotavapped and the residue purified on ISCO to give product as a white solid. (126 mg, 57%); mp 125-126° C. $^1$H NMR (CDCl3) (400 MHz) δ 7.34 (m, 10), 5.36 (m, 1H), 5.23 (d, 1H, J=4), 5.09 (s, 4H), 4.72 (m, 1H), 3.72 (m, 1H), 3.21 (m, 4H), 1.45 (m, 4H), 1.42 (s, 9H); 13 C δ 157.0, 156.5, 156.1, 136.4, 128.5, 128.1, 128.07, 128.0, 79.1, 66.8, 66.7, 51.7, 45.0, 40.1, 29.5, 28.4, 26.4

Intermediate d

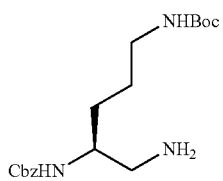 [SMILES: CC(C)(C)OC(=O)NCCC[C@@H](CN)NC(=O)OCc1ccccc1]

Benzyl tert-butyl (5-aminopentane-1,4-diyl)(S)-dicarbamate

The phthalimide (340 mg, 0.71 mmol) formed was dissolved in methanol (20 mL) and hydrazine monohydrate (0.07 mL, 1.41 mmol) was added. The reaction mixture was then refluxed for 2 hours and cooled to room temperature. The precipitate formed was filtered and methanol used to wash the filtrate. The filtrate was rotavapped and the remaining solid purified on ISCO (0-10% Methanol/DCM+1% NH4OH) to give product as a colorless oil. (164 mg, 66%)%); $^1$H NMR (CDCl3) (400 MHz) δ 7.25 (m, 5H), 5.41 (d, 1H, J=8), 5.00 (s, 1H), 4.84 (brs, 1H); 3.50 (m, 1H), 3.01 (m, 2H), 2.61 (m, 2H), 1.40 (m, 4H), 1.36 (s, 9H); $^{13}$C (CDCl3)(100 MHz) δ 156.6, 156.0, 136.6, 128.4, 128.1, 128.0, 78.9, 66.6, 53.2, 45.7, 40.2, 29.7, 28.4, 26.6, 25.0, 24.9

Intermediate e

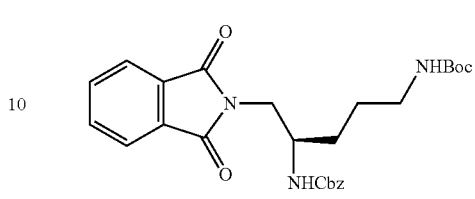

Benzyl tert-butyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was rotavapped and residue purified on ISCO (0-70% Ethyl acetate/hexane) to give product as a white solid. (340 mg, 69%); mp 74-76° C.; 1H NMR (CDCl3) (400 MHz) δ 7.82 (m, 2H), 7.71 (m, 2H), 7.27 (m, 5H), 5.18 (brs, 1H), 4.96 (m, 2H), 4.67 (brs, 1H), 4.02 (m, 1H) 3.75 (m, 2H), 3.14 (m, 2H), 1.55 (m, 4H), 1.44 (s, 9H); 13 C δ 168.4, 156.3, 156.0, 136.6, 133.9, 131.8, 128.4, 128.3, 127.8, 127.7, 123.3, 78.9, 66.3, 60.3, 50.7, 41.9, 40.2, 29.9, 28.4, 26.4

Intermediate f

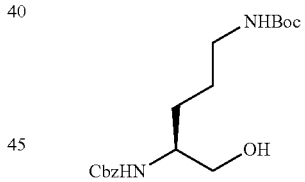

Benzyl tert-butyl (5-hydroxypentane-1,4-diyl)(S)-dicarbamate

To a solution of methyl (S)-2-(((benzyloxy)carbonyl)amino)-5-((tert-butoxycarbonyl)-amino)pentanoate (431 mg, 1.13 mmol) in THF (5 mL)/Ethanol (1 mL) was added LiBH4 (32 mg, 1.47 mmol) at 0° C. The mixture was stirred at that temperature for 30 minutes and warmed to room temperature and stirred for overnight. The reaction mixture was poured into water and extracted with ethyl acetate. The combine organic layers were washed with brine and dried over sodium sulfate and concentrated. It was purified on ISCO (0-70% ethyl acetate/hexane to give product as a colorless oil. (385 mg, 97%); 1H NMR (CDCl3) (400 MHz) δ 7.28 (m, 5H), 5.02 (s, 3H), 3.60 (m, 4H), 3.04 (m, 2H), 1.47 (m, 4H), 1.36 (m, 9H); 13 C S 156.6, 156.1, 136.4, 128.5, 128.1, 128.0, 79.3, 66.8, 65.0, 62.7, 52.9, 52.4, 40.3, 29.8, 28.4, 26.7, 26.0

Intermediate g

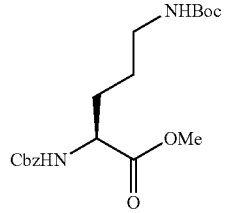 [SMILES: COC(=O)[C@H](CCCNC(=O)OC(C)(C)C)NC(=O)OCc1ccccc1]

Methyl (S)-2-(((benzyloxy)carbonyl)amino)-5-((tert-butoxycarbonyl)amino)pentanoate Cbz-L-ornithine (Boc) acid (1 g, 2.73 mmol) was dissolved in DMF (5 mL) and $K_2CO_3$ (452 mg, 3.26 mmol). The reaction was cooled to 0° C. and methyl iodide (775 mg, 5.46 mmol) was added. The reaction was allowed to warm to room temperature and stirred at the temperature overnight. Then the reaction mixture was washed with saturated sodium bicarbonate solution and extracted with ethyl acetate. The combined organic layers were washed with brine, dried over sodium sulfate, concentrated and purified on ISCO (0-60% ethyl acetate/Hexane) to give product as a colorless oil. (761 mg, 73%); $^1$H NMR δ 7.19 (s, 5H), 6.06 (d, 1H, J=8), 5.12 (brs, 1H), 4.94 (s, 2H), 4.17 (m, 1H), 3.55 (s, 3H), 2.94 (m, 2H), 1.69 (m, 1H), 1.55 (m, 1H), 1.40 (m, 2H), 1.27 (s, 9H); $^{13}$C δ 172.7, 156.0, 155.9, 136.3, 128.2, 128.1, 127.9, 127.8, 78.6, 67.2, 66.5, 53.7, 39.8, 29.2, 28.2, 25.9.

Example 3. Preparation of (S)—N1-(1,5-diphenylpentan-3-yl)butane-1,2,4-triamine 3 TFA

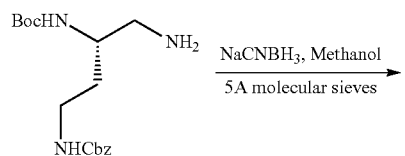

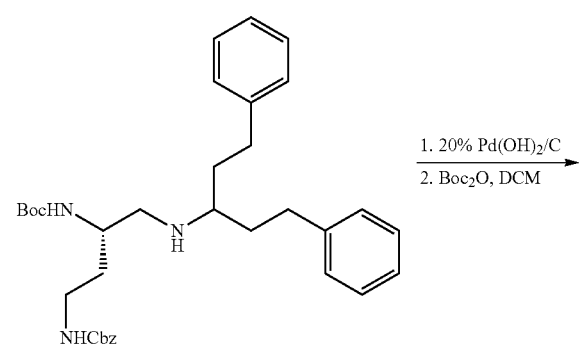

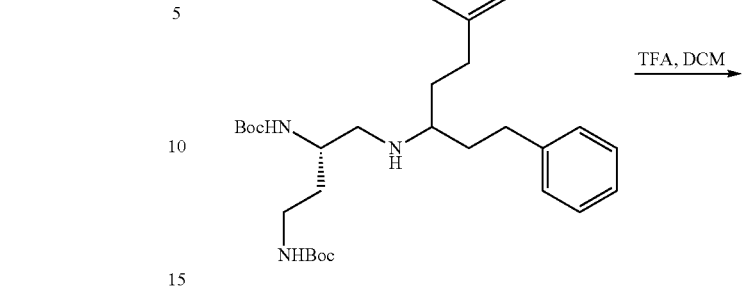

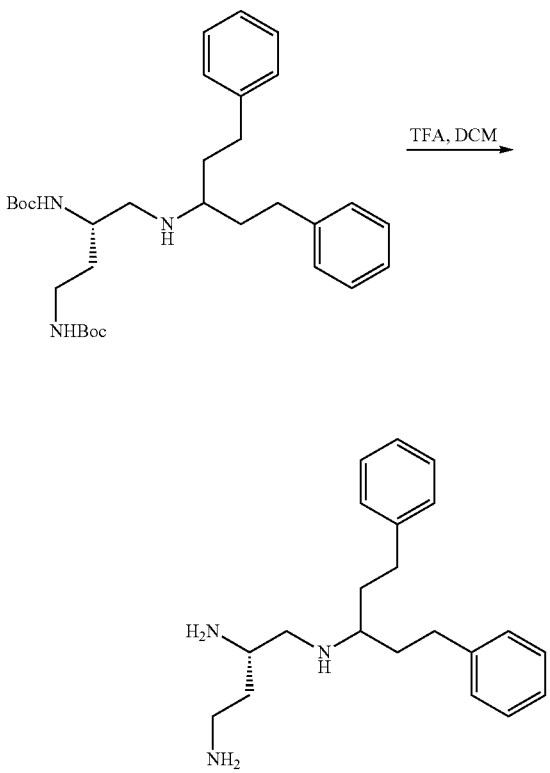

(S)—N$^1$-(1,5-diphenylpentan-3-yl)butane-1,2,4-triamine 3TFA

Di-tert-butyl (4-((1,5-diphenylpentan-3-yl)amino)butane-1,3-diyl)(S)-dicarbamate (22 mg, 0.03 mmol) was dissolved in dichloromethane (1 mL) and cooled to 0° C. Trifluoroacetic acid (0.5 mL) was added and reaction stirred at 0° C. for 2 hours. The solvents were evaporated and the residue redissolved in methanol. The methanol was evaporated and this was repeated 3 times. The residue was dried in vacuo to obtain product as a salt of TFA (colorless oil, 20.3 mg, 94%). $^1$H NMR (CD$_3$OD) δ 7.28 (M, 10H), 3.80 (m, 1H), 3.39 (m, 3H), 3.15 (m, 2H), 2.78 (m, 4H), 2.14 (m, 6H)

The requisite intermediates were prepared as described in the following paragraphs.

Intermediate a

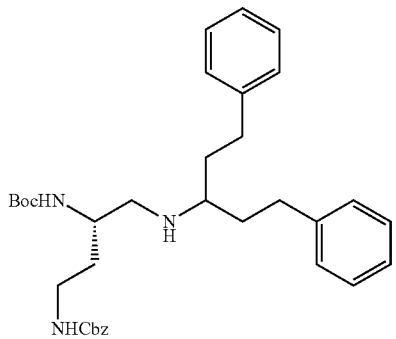 [SMILES: CC(C)(C)OC(=O)N[C@@H](CCNC(=O)OCc1ccccc1)CNC(CCc1ccccc1)CCc1ccccc1]

Di-tert-butyl (4-((1,5-diphenylpentan-3-yl)amino)butane-1,3-diyl)(S)-dicarbamate Benzyl tert-butyl (4-((1,5-diphenylpentan-3-yl)amino)butane-1,3-diyl)(S)-dicarbamate (128 mg, 0.23 mmol) was dissolved in ethanol (10 mL) and 20% Pd(OH)$_2$/C (60 mg) was added. Reaction was stirred under a hydrogen atmosphere for overnight. The catalyst was removed by filtration and washed with 20% Methanol/dichloromethane. The solvent was then rotavapped and the residue dissolved in dichloromethane (10 mL). Boc$_2$O was added and the reaction stirred at room temperature for 1 hour. The solvent was removed by evaporation and the residue purified on ISCO (0-20% Ethyl acetate/hexane) to give product as a colorless oil. (22.8 mg, 30%); $^1$H NMR (CDCl$_3$) δ 5.48 (m, 1H), 3.61 (m, 2H), 3.36 (m, 2H, 2.89 (m, 2H), 2.50 (m, 4H), 1.67 (m, 8H), 1.35 (s, 9H), 1.28 (s, 9H); $^{13}$C NMR (CDCl$_3$) δ 156.8, 156.2, 141.2, 128.5, 128.4, 128.3, 125.8, 80.4, 78.8, 36.9, 34.9, 32.7, 28.5, 28.4, 28.3.

Intermediate b

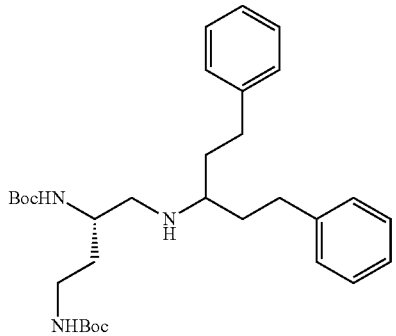 [SMILES: CC(C)(C)OC(=O)NCC[C@@H](CNC(CCc1ccccc1)CCc1ccccc1)NC(=O)OC(C)(C)C]

Benzyl tert-butyl (4-((1,5-diphenylpentan-3-yl)amino)butane-1,3-diyl)(S)-dicarbamate To benzyl tert-butyl (4-aminobutane-1,3-diyl)(S)-dicarbamate (100 mg, 0.3 mmol) in methanol (10 mL) was added 1,5-diphenylpentan-3-one (85 mg, 0.36 mmol) and 5 A molecular sieves. Sodium cyanoborohydride (56 mg, 0.89 mmol) was added. The reaction was heated at 70° C. for 7 hours, then cooled to room temperature. The molecular sieves were filtered off and washed with methanol. The methanol was evaporated and the residue was dissolved in ethyl acetate. The organic layer was quenched with saturated ammonium chloride solution and washed with saturated sodium bicarbonate, then brine. The organic layer was dried over sodium sulfate, concentrated and purified on ISCO (10% Methanol/Dichloromethane) to give product as a colorless oil. (74 mg, 45%); $^1$H NMR (CDCl$_3$) δ 7.18 (m, 15H), 5.64 (brs, 1H), 5.01 (m, 3H), 3.60 (brs, 1H), 3.36 (m, 1H), 2.98 (m, 1H), 2.59 (m, 6H), 1.66 (m, 5H), 1.36 (s, 10H), 1.18 (m, 2H); $^{13}$C NMR (CDCl$_3$) 156.70, 141.8, 141.6, 136.7, 128.53, 128.5, 128.36, 128.33, 128.0, 126.0, 125.9, 80.0, 66.5, 57.0, 50.4, 47.8, 37.6, 35.2, 34.9, 33.6, 31.9, 28.3, 22.0

Example 4. Preparation of (S)—N4-(1,5-diphenylpentan-3-yl)butane-1,2,4-triamine 3 TFA

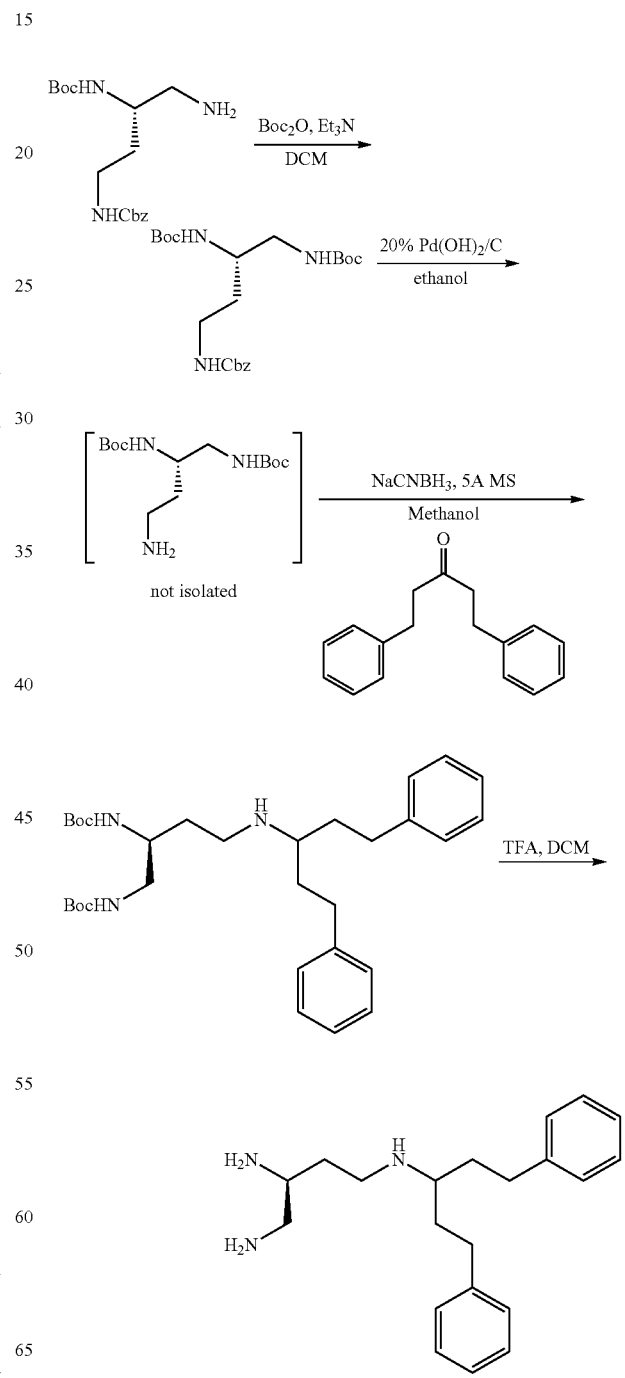

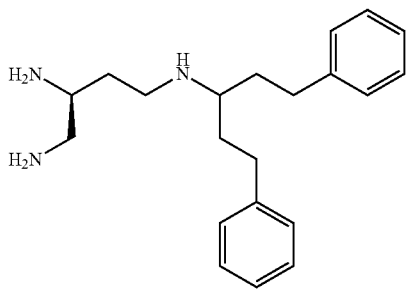 [SMILES: NC[C@@H](N)CCNC(CCc1ccccc1)CCc1ccccc1]

(S)—N⁴-(1,5-diphenylpentan-3-yl)butane-1,2,4-triamine 3 TFA

Di-tert-butyl (4-((1,5-diphenylpentan-3-yl)amino)butane-1,2-diyl)(R)-dicarbamate (19 mg, 0.04 mmol) was dissolved in DCM (1 mL) and trifluoroacetic acid (0.5 mL) was added. The reaction was stirred at room temperature for 2 hours. The solvent was removed through evaporation and multiple evaporation was done with methanol. The oil obtained was dried in vacuo. (22 mg, 100%); $^1$H (400 MHz) (CD$_3$OD) δ 7.15 (m, 10H), 3.65 (m, 1H), 3.16 (m, 5H), 2.64 (t, 4H, J=8), 2.12 (m, 2H), 1.99 (m, 4H); $^{13}$C NMR (100 MHz) (CD$_3$OD) δ141.6, 129.7, 129.4, 127.4, 59.6, 42.3, 41.9, 32.9, 32.8, 31.9, 28.6

The requisite intermediates were prepared as described in the following paragraphs.

Intermediate a

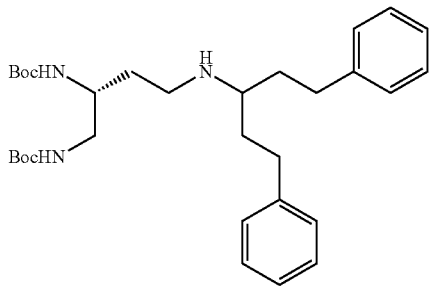 [SMILES: CC(C)(C)OC(=O)NC[C@@H](CCNC(CCc1ccccc1)CCc1ccccc1)NC(=O)OC(C)(C)C]

Di-tert-butyl (4-((1,5-diphenylpentan-3-yl)amino)butane-1,2-diyl)(R)-dicarbamate Benzyl di-tert-butyl butane-1,2,4-triyl(S)-tricarbamate (140 mg, 0.32 mmol) was dissolved in ethanol (10 mL) and 20% Pd(OH)$_2$/C (40 mg) was added. Reaction was stirred under nitrogen atmosphere overnight. The catalyst was filter and the residue washed with 20% methanol/DCM. The solvents were removed by evaporation and reaction taking to the next step with no purification. The crude di-tert-butyl (4-aminobutane-1,2-diyl)(S)-dicarbamate was dissolved in methanol (10 mL) and 1,5-diphenylpentan-3-one (57 mg, 0.24 mmol) and 5 A molecular sieves were added. Then sodium cyanoborohydride (38 mg, 0.6 mmol) was added and reaction was stirred at 70° C. for 7 hours. The molecular sieves were then filtered off and the residue washed with methanol. The methanol was evaporated and the residue was dissolved in ethylacetate. The organic layer was quenched with saturated ammonium chloride solution and washed with saturated sodium bicarbonate, then brine. The organic layer was dried over sodium sulfate, concentrated and purified on ISCO (10% Methanol/Dichloromethane) to give product as a colorless oil. (48.6 mg, 47%); $^1$H NMR (CDCl$_3$) δ 7.15 (m, 10H), 5.83 (brs, 1H), 5.07 (brs, 1H), 3.60 (brs, 1H), 3.64 (m, 1H), 3.15 (m, 2H), 2.60 (m, 7H), 1.73 (m, 4H), 1.36 (s, 9H), 1.34 (m, 2H), 1.32 (s, 9H); $^{13}$C NMR (CDCl$_3$) δ 156.8, 142.0, 128.4, 128.3, 125.8, 79.5, 79.3, 56.8, 50.3, 44.8, 42.9, 35.1, 32.4, 31.9, 32.8, 31.3, 29.6, 28.4, 28.3.

Intermediate b

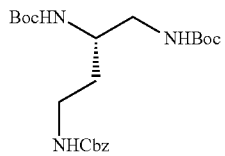

Benzyl di-tert-butyl butane-1,2,4-triyl(S)-tricarbamate

Benzyl tert-butyl (4-aminobutane-1,3-diyl)(S)-dicarbamate (280 mg, 0.83 mmol) was dissolved in dichloromethane (10 mL) and trimethylamine (0.17 mL, 1.25 mmol) was added. Boc$_2$O (543 mg, 2.49 mmol) was added and the reaction was stirred at room temperature overnight. The reaction mixture was then dissolved in water and extracted with DCM. The organic layer was dried over sodium sulfate and filtered. The filtrate was rotavapped and the residue purified on ISCO column (50% Ethyl acetate/hexane) to give product as a colorless oil (190 mg, 52%); $^1$H NMR (400 MHz) (CDCl$_3$) δ 7.31 (m, 5H), 5.76 (brs, 1H), 5.11 (m, 4H), 3.68 (m, 1H), 3.45 (m, 1H), 3.16 (m, 2H), 3.00 (m, 1H), 1.68 (m, 1H), 1.43 (s, 9H), 1.42 (m, 1H), 1.41 (s, 9H); $^{13}$C NMR (100 MHz) (CDCl$_3$) δ 156.7, 156.5, 136.7, 128.4, 128.0, 127.9, 79.5, 79.4, 66.4, 49.4, 44.4, 37.5, 33.2, 28.4, 28.3

Example 5. Preparation of (S)—N$^1$-(1,5-diphenylpentan-3-yl)pentane-1,3,5-triamine 3 TFA

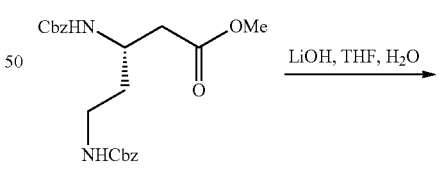

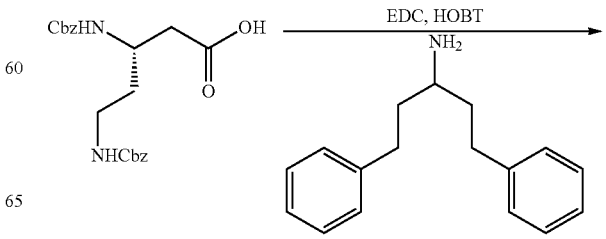

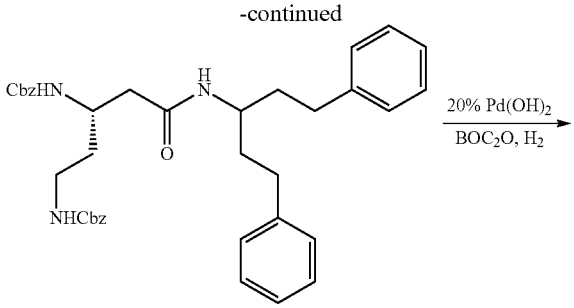

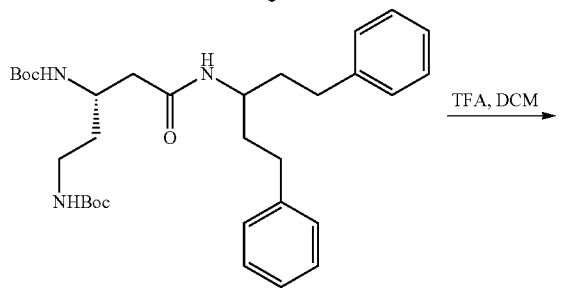

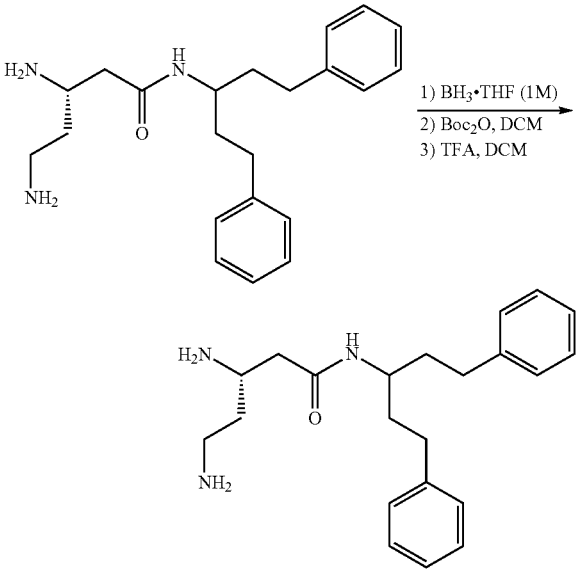

(S)—N¹-(1,5-Diphenylpentan-3-yl)pentane-1,3,5-triamine 3 TFA (S)-3,5-Diamino-N-(1,5-diphenylpentan-3-yl)pentanamide (77 mg, 0.14 mmol) was dissolved in 10 mL of THF and BH$_3$.THF (2 mL) and the mixture was heated at 83° C. for overnight. Then methanol (10 mL) was added and the reaction mixture was stirred at that same temperature for 2 hours. Then water (1 mL) was added and the reaction cooled to room temperature. Solvents presents were then rotavapped and redissolved in DCM, dried with sodium sulfate and organic layer filtered and solvent removed to give an oil residue. The residue was redissolved in DCM and Boc$_2$O was added and reaction stirred for 2 hrs. Workup was done by phase extraction with water and ethyl acetate. The organic layer was dried over sodium sulfate and filtered and rotavapped. The residue was purified on ISCO (0-30% Ethyl acetate/Hexane) to give di-tert-butyl (5-((tert-butoxycarbonyl)(1,5-diphenylpentan-3-yl)amino)pentane-1,3-diyl)(S)-dicarbamate as a colorless oil (15 mg). The di-tert-butyl (5-((tert-butoxycarbonyl)(1,5-diphenylpentan-3-yl)amino)pentane-1,3-diyl)(S)-dicarbamate (11 mg) was dissolved in DCM (1 mL) and TFA (0.5 mL). The reaction mixture was stirred at room temperature for 2 hrs. The solvents were removed and residue was vacuum dried to obtain product (TFA salt) as a colorless oil; $^1$H NMR (400 MHz) (MeOD) δ 7.16 (m, 10H), 3.36 (m, 2H), 3.15 (m, 2H), 3.02 (m, 4H), 1.98 (m, 8H)

The requisite intermediates were prepared as described in the following paragraphs.

Intermediate a

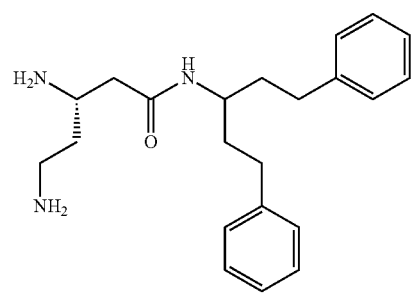 [SMILES: NCC[C@H](N)CC(=O)NC(CCc1ccccc1)CCc1ccccc1]

(S)-3,5-Diamino-N-(1,5-diphenylpentan-3-yl)pentanamide

Di-tert-butyl (5-((1,5-diphenylpentan-3-yl)amino)-5-oxopentane-1,3-diyl)(S)-dicarbamate (78 mg, 0.14 mmol) was dissolved in DCM (5 mL) and TFA (2.5 mL) at 0° C. Reaction was stirred at that temperature for 2 hrs under nitrogen. The solvents were removed to obtain product as a TFA salt, colorless oil. (77 mg, 100%); $^1$H NMR (400 MHz) (MeOD) δ 7.09 (m, 10H), 3.84 (m, 1H), 3.58 (m, 1H), 3.01 (m, 2H), 2.54 (m, 6H), 1.98 (m, 2H), 1.70 (m, 4H); $^{13}$C NMR (100 MHz) (CDCl$_3$) δ 171.2, 143.2, 143.1, 129.4, 126.8, 50.4, 47.7, 37.9, 37.8, 37.2, 37.0, 33.4, 31.7.

Intermediate b

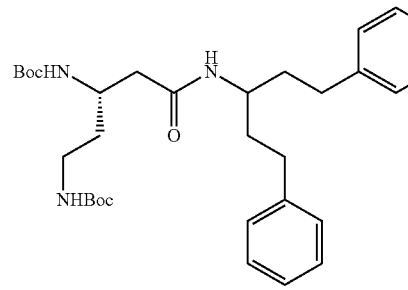

Di-tert-butyl (5-((1,5-diphenylpentan-3-yl)amino)-5-oxopentane-1,3-diyl)(S)-dicarbamate Dibenzyl (5-((1,5-diphenylpentan-3-yl)amino)-5-oxopentane-1,3-diyl)(S)-dicarbamate (170 mg, 0.27 mmol) was dissolved in ethanol (15 mL), then 20% Pd(OH)$_2$/C (50 mg) and Boc$_2$O (176 mg, 0.81 mmol) was added. Reaction was stirred under hydrogen atmosphere for overnight. Then the catalyst was filter and the filtrate concentrated and purified on ISCO (0-10 MeOH/DCM) to give product as a white solid; $^1$H NMR (400 MHz) (CDCl$_3$) δ 7.24 (m, 1 OH), 5.83 (m, 2H), 5.31 (brs, 1H), 4.07 (m, 1H), 3.91 (m, 1H), 3.40 (m, 1H), 2.97 (m, 1H), 2.58 (m, 5H), 2.29 (dd, 1H, J=8.16), 1.77 (m, 6H), 1.46 (s, 9H), 1.42 (s, 9H); $^{13}$C NMR (100 MHz) (CDCl$_3$) δ 170.7, 156.1, 141.7, 141.6, 128.5, 128.4, 128.38, 128.33, 125.9, 79.3, 79.1, 49.2, 45.5, 37.1, 36.9, 35.0, 32.5, 32.4, 28.5, 28.4, 28.3

Intermediate c

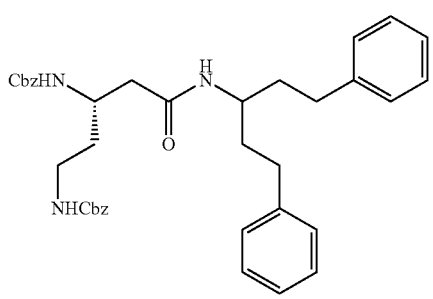 [SMILES: O=C(C[C@H](CCNC(=O)OCc1ccccc1)NC(=O)OCc1ccccc1)NC(CCc1ccccc1)CCc1ccccc1]

Dibenzyl (5-((1,5-diphenylpentan-3-yl)amino)-5-oxopentane-1,3-diyl)(S)-dicarbamate (S)-3,5-Bis(((benzyloxy)carbonyl)amino)pentanoic acid (150 mg, 0.375 mmol) was dissolved in DMF (5 mL), then EDC (143 mg, 0.75 mmol) and HOBT (101 mg, 0.75 mmol) was added. Reaction was stirred under nitrogen for 5 minutes. Then 1,5-diphenylpentan-3-amine (99 mg, 0.41 mmol) and 2,6-lutidine (0.14 mL, 1.24 mmol) was added sequentially. The reaction was stirred at room temperature overnight. On completion of the reaction, the reaction mixture was diluted with ethyl acetate and the organic layer washed with water, saturated sodium bicarbonate, 5% hydrochloric acid solution, water and brine. The organic layer was dried over sodium sulfate, concentrated to give product as a yellow solid. (171 mg, 73%); %); $^1$H NMR (400 MHz) (CDCl$_3$) δ 7.17 (m, 20H), 6.07 (d, 1H, J=8); 5.44 (m, 2H), 5.00 (m, 4H), 3.94 (m, 2H), 3.38 (m, 1H), 2.95 (m, 1H), 2.54 (m, 5H), 2.29 (m, 1H), 1.70 (m, 6H); $^{13}$C NMR (100 MHz) (CDCl$_3$) δ 156.7, 141.5, 136.6, 136.4, 128.5, 128.4, 128.3, 128.0, 127.9, 126.0, 66.7, 66.6, 49.3, 37.0, 36.8, 32.4, 32.3

Intermediate d

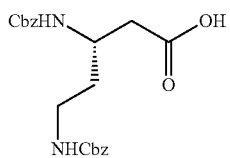 [SMILES: O=C(O)C[C@H](CCNC(=O)OCc1ccccc1)NC(=O)OCc1ccccc1]

(S)-3,5-Bis(((benzyloxy)carbonyl)amino)pentanoic acid

Methyl (S)-3,5-bis(((benzyloxy)carbonyl)amino)pentanoate (236 mg, 0.56 mmol) was dissolved in THF/water (12 mL) (5:1) and treated with LiOH.H$_2$O (28 mg, 0.67 mmol) at 0° C. under nitrogen. Reaction mixture was stirred at room temperature overnight. Then 1N HCl was added and THF removed by rotary evaporation. A white solid which had precipitated was filtered. The residue was saved and the filtrate was extracted with ethyl acetate. The organic layer was dried over sodium sulfate and solvent evaporated. The precipitated solid was added and the combined residue was dried on a vacuum pump to give product as a white solid. (150 mg, 67%); $^1$H NMR (400 MHz) (CD$_3$OD) δ 7.24 (m, 10H), 4.96 (s, 4H), 3.92 (m, 1H); 3.13 (m, 1H), 2.99 (m, 1H), 2.40 (d, 2H, J=4); 1.67 (m, 1H), 1.55 (m, 1H); $^{13}$C NMR (100 MHz) (CD$_3$OD) δ 158.8, 138.4, 129.4, 128.9, 128.8, 128.7, 67.4, 47.2, 40.3, 38.7, 35.6

Example 6. Preparation of (S)—N1-(2-phenethyl-4-phenylbutyl)pentane-1,3,5-triamine 3 TFA

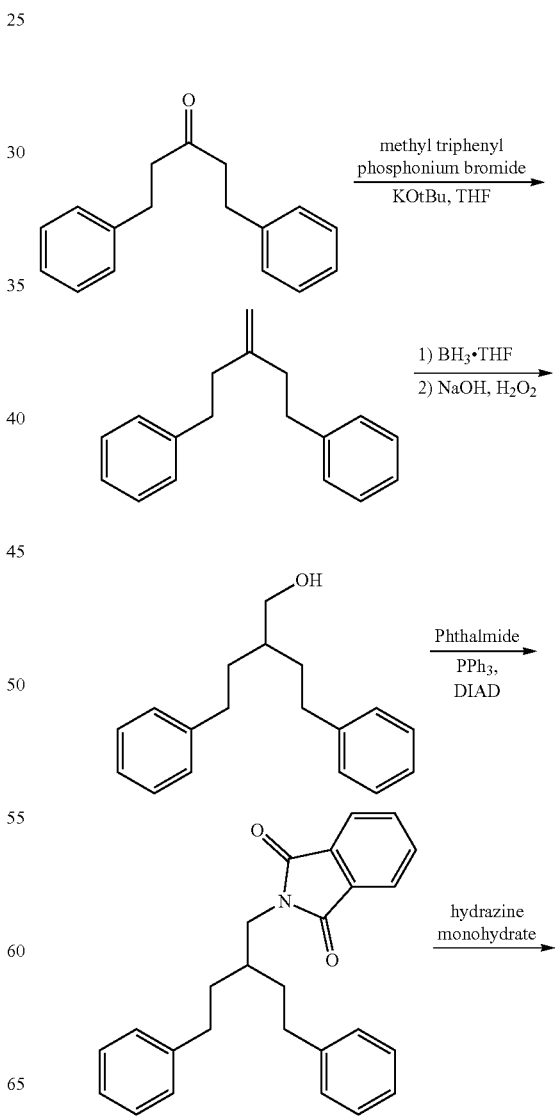

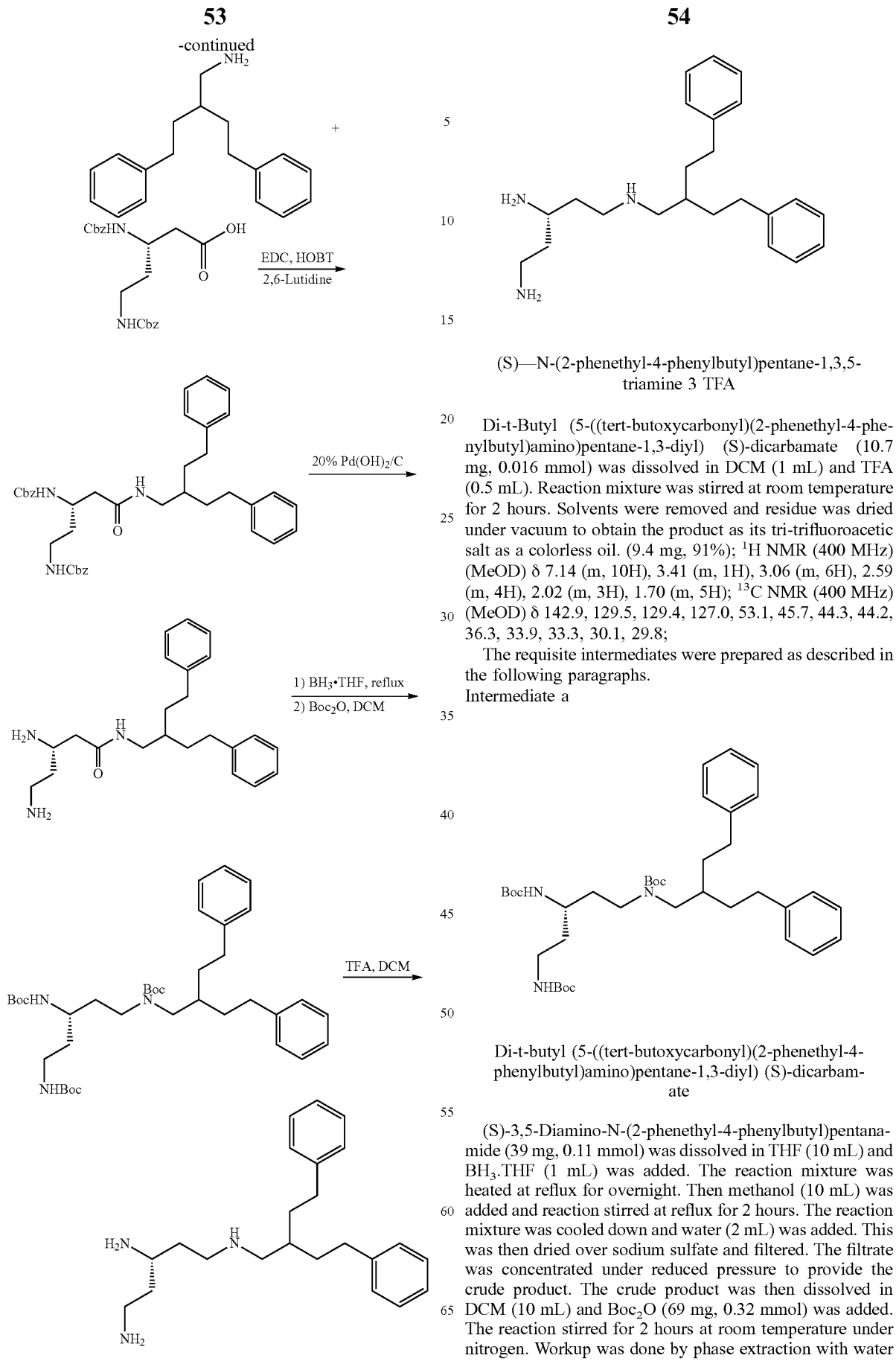

(S)—N-(2-phenethyl-4-phenylbutyl)pentane-1,3,5-triamine 3 TFA

Di-t-Butyl (5-((tert-butoxycarbonyl)(2-phenethyl-4-phenylbutyl)amino)pentane-1,3-diyl) (S)-dicarbamate (10.7 mg, 0.016 mmol) was dissolved in DCM (1 mL) and TFA (0.5 mL). Reaction mixture was stirred at room temperature for 2 hours. Solvents were removed and residue was dried under vacuum to obtain the product as its tri-trifluoroacetic salt as a colorless oil. (9.4 mg, 91%); $^1$H NMR (400 MHz) (MeOD) δ 7.14 (m, 10H), 3.41 (m, 1H), 3.06 (m, 6H), 2.59 (m, 4H), 2.02 (m, 3H), 1.70 (m, 5H); $^{13}$C NMR (400 MHz) (MeOD) δ 142.9, 129.5, 129.4, 127.0, 53.1, 45.7, 44.3, 44.2, 36.3, 33.9, 33.3, 30.1, 29.8;

The requisite intermediates were prepared as described in the following paragraphs.

Intermediate a

Di-t-butyl (5-((tert-butoxycarbonyl)(2-phenethyl-4-phenylbutyl)amino)pentane-1,3-diyl) (S)-dicarbamate (S)-3,5-Diamino-N-(2-phenethyl-4-phenylbutyl)pentanamide (39 mg, 0.11 mmol) was dissolved in THF (10 mL) and BH$_3$.THF (1 mL) was added. The reaction mixture was heated at reflux for overnight. Then methanol (10 mL) was added and reaction stirred at reflux for 2 hours. The reaction mixture was cooled down and water (2 mL) was added. This was then dried over sodium sulfate and filtered. The filtrate was concentrated under reduced pressure to provide the crude product. The crude product was then dissolved in DCM (10 mL) and Boc$_2$O (69 mg, 0.32 mmol) was added. The reaction stirred for 2 hours at room temperature under nitrogen. Workup was done by phase extraction with water and ethyl acetate. The organic layer was dried over sodium sulfate and filtered and concentrated under reduced pressure. The residue was purified on an ISCO chromatograph with silica using (0-30% ethyl acetate/hexane) to give product as a colorless oil. (34 mg, 49%); $^1$H NMR (400 MHz) (CDCl$_3$) δ 7.14 (m, 10H), 3.10 (m, 6H), 2.54 (m, 4H), 1.28 (m, 37H); $^{13}$C NMR (100 MHz) (CDCl$_3$) δ 155.7, 142.5, 128.3, 125.7, 79.4, 79.2, 44.6, 43.8, 33.1, 32.9, 32.7, 29.6, 28.5, 28.5, 28.4, 28.0.

Intermediate b

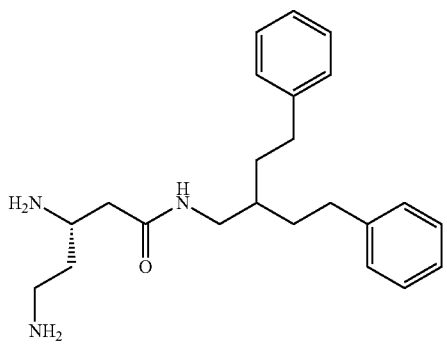 [SMILES: NCC[C@H](N)CC(=O)NCC(CCc1ccccc1)CCc1ccccc1]

(S)-3,5-Diamino-N-(2-phenethyl-4-phenylbutyl) pentanamide

Dibenzyl (5-oxo-5-((2-phenethyl-4-phenylbutyl)amino) pentane-1,3-diyl)(S)-dicarbamate (90 mg, 0.14 mmol) was dissolved in ethanol (10 mL) and 20% Pd(OH)$_2$/C (40 mg) was added. The reaction mixture was purged and stirred under hydrogen atmosphere for overnight. Then the catalyst was filtered off and washed with 20% methanol/DCM. The solvent was concentrated under reduced pressure and the residue dried on the vacuum to obtain the product as a colorless oil (50.2 mg, 97%); $^1$H NMR (400 MHz) (CDCl$_3$) δ 7.14 (m, 11H), 3.22 (m, 3H), 2.85 (m, 5H), 2.56 (m, 5H), 2.18 (m, 2H), 1.57 (m, 7H); $^{13}$C NMR (100 MHz) (CDCl$_3$) δ 171.7, 171.6, 142.4, 142.3, 128.4, 128.3, 125.84, 125.8, 67.2, 53.1, 47.8, 45.3, 43.2, 43.0, 41.9, 41.6, 37.2, 37.1, 33.9, 33.8, 33.7, 33.0, 32.9, 32.6, 22.8.

Intermediate c

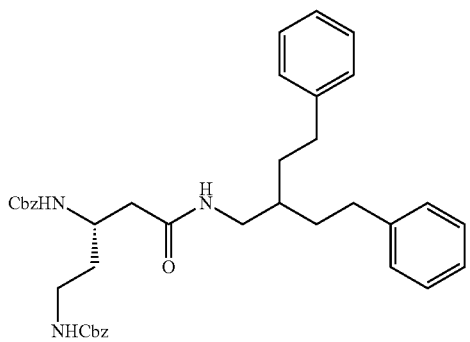 [SMILES: O=C(C[C@H](CCNC(=O)OCc1ccccc1)NC(=O)OCc1ccccc1)NCC(CCc1ccccc1)CCc1ccccc1]

Dibenzyl (5-oxo-5-((2-phenethyl-4-phenylbutyl) amino)pentane-1,3-diyl)(S)-dicarbamate (S)-3,5-Bis(((benzyloxy)carbonyl)amino)pentanoic acid (115 mg, 0.29 mmol) was dissolved in DMF (5 mL), EDC (110 mg, 0.58 mmol) and HOBT (78 mg, 0.58 mmol) were added. The reaction was stirred at room temperature for 5 minutes. 2-Phenethyl-4-phenylbutan-1-amine (84 mg, 0.33 mmol) was added followed by 2,6-lutidine (0.11 mL, 0.99 mmol). The reaction was stirred at room temperature overnight. The reaction mixture was diluted with ethyl acetate and washed with water, saturated sodium bicarbonate, 5% HCl, water and brine. The combined organic layer was dried over sodium sulfate, concentrated and purified by using an ISCO chromatograph on silica using ethyl acetate/hexane (0-60%) to give product as a white solid. MP 169-170° C.; $^1$H NMR (400 MHz) (CDCl$_3$) δ 7.28 (m, 20H), 6.32 (brs, 1H), 5.99 (brs, 1H), 5.69 (brs, 1H), 5.08 (m, 4H), 3.98 (m, 1H), 3.41 (m, 1H), 3.29 (m, 2H), 2.99 (m, 1H), 2.57 (m, 5H), 2.29 (m, 1H), 1.66 (m, 7H); $^{13}$C NMR (100 MHz) (CDCl$_3$) δ 171.1, 156.6, 142.2, 136.6, 136.5, 128.5, 128.4, 128.3, 128.1, 128.0, 127.9, 125.9, 66.6, 66.5, 46.0, 42.1, 40.0, 37.5, 37.2, 34.6, 33.6, 33.5, 32.9, 32.8.

Intermediate d

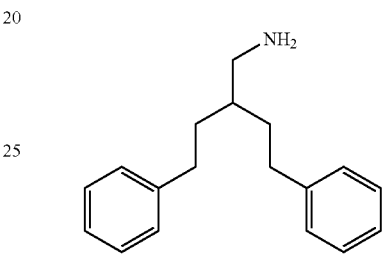

2-Phenethyl-4-phenylbutan-1-amine

Hydrazine monohydrate (120 μL, 2.4 mmol) was added to a solution of 2-(2-phenethyl-4-phenylbutyl)isoindoline-1,3-dione (460 mg, 1.2 mmol) in methanol (15 mL) at room temperature. Then the reaction stirred under reflux for 2 hours. The completed reaction mixture was cooled to room temperature and the white precipitate filtered. The filtered material was washed with cold methanol, the filtrate was concentrated and purified on an ISCO chromatography and purified on silica using (0-10% MeOH/DCM+1% NH$_4$OH) to give the desired product as a colorless oil. (223 mg, 74%); $^1$H NMR (400 MHz) (CDCl$_3$) δ 7.36 (m, 4H), 7.26 (m, 6H), 2.80 (d, 2H, J=4), 2.71 (t, 4H, J=8), 1.75 (m, 4H), 1.55 (m, 1H), 1.30 (brs, 2H); $^{13}$C NMR (100 MHz) (CDCl$_3$) δ 142.7, 128.43, 128.41, 125.8, 45.0, 40.2, 33.4, 33.19.

Intermediate e

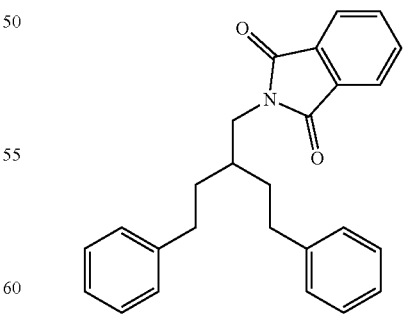

2-(2-Phenethyl-4-phenylbutyl)isoindoline-1,3-dione

Triphenylphosphine (570 mg, 2.17 mmol) and phthalimide (319 mg, 2.17 mmol) were dissolved in THF (6 mL) at 0° C. under nitrogen. Then 2-phenethyl-4-phenylbutan-1-ol (460 mg, 1.80 mmol) in THF (2 mL). DIAD (0.43 mL, 2.17 mmol) was added dropwise to the reaction mixture. The reaction was allowed to stir for 30 minutes at 0° C. and overnight at room temperature. Then the solvents were rotavapped and residue purified on an ISCO chromatograph with silica using (0-30% ethyl acetate/hexane) to give product as a white powder. (630 mg, 91%); MP 75-76° C.; $^1$H NMR (400 MHz) (CDCl$_3$) δ 7.91 (m, 2H), 7.74 (m, 2H), 7.32 (m, 10H), 3.82 (d, 2H, J=8), 2.83 (m, 4H), 2.15 (m, 1H), 1.81 (m, 4H); $^{13}$C NMR (100 MHz) (CDCl$_3$) δ 168.6, 142.7, 142.4, 142.1, 133.9, 132.4, 132.1, 128.9, 128.8, 128.7, 128.5, 128.4, 128.3, 128.2, 126.1, 125.9, 125.5, 123.2, 41.6, 36.9, 33.7, 32.8

Intermediate f

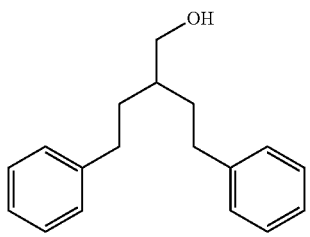 [SMILES: OCC(CCc1ccccc1)CCc1ccccc1]

2-Phenethyl-4-phenylbutan-1-ol

To a solution of (3-methylenepentane-1,5-diyl)dibenzene (650 mg, 2.75 mmol) in THF (5 mL), cooled to 0° C. was added BH$_3$THF (4.1 mL, 4.1 mmol). The reaction was stirred at that temperature for 30 minutes, then warmed to room temperature and stirred for an additional 2 hours under nitrogen. Then the reaction was cooled again to 0° C., 3 M NaOH (4.6 mL) and 30% H$_2$O$_2$ (1.4 mL) were added. The reaction was stirred at 0° C. for 30 minutes and heated at 60° C. for an additional hour. Solvents were removed under reduced pressure and the resulting residue diluted with water and extracted with ethyl acetate. The combined organic layers were washed with water, brine, dried over sodium sulfate, concentrated and purified on an ISCO chromatograph with silica using 0-40% ethyl acetate/hexane to give the product as a colorless oil. (538 mg, 77%); $^1$H NMR (400 MHz) (CDCl$_3$) δ 7.29 (m, 10H), 3.69 (d, 2H, J=8), 2.71 (m, 4H, J=8), 1.72 (m, 5H), 1.47 (brs, 1H); $^{13}$C NMR (100 MHz) (CDCl$_3$) δ 142.5, 128.41, 128.40, 125.8, 65.3, 39.7, 33.2, 32.8

Intermediate g

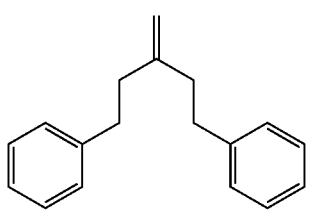 [SMILES: C=C(CCc1ccccc1)CCc1ccccc1]

(3-Methylenepentane-1,5-diyl)dibenzene

To a suspension of methyl triphenylphosphonium bromide (2,397 mg, 6.7 mmol) in THF (8 mL) at room temperature was added portion wise potassium t-butoxide (848 mg, 7.56 mmol) under nitrogen. The mixture was stirred at that temperature for 3 hours. Then a solution of 1,5-diphenylpentan-3-one (1,000 mg, 4.2 mmol) in THF (2 mL) was added dropwise. The mixture was stirred for overnight, the mixture was then concentrated under reduced pressure and ice water added to the residue. The aqueous solution was extracted with ethyl acetate. The organic layer was then separated, washed with brine and dried over sodium sulfate. The filtrate was then concentrated and purified on an ISCO chromatograph on silica using 0-5% ethyl acetate/hexane to give the product as a colorless oil. (806 mg, 81%); $^1$H NMR (400 MHz) (CDCl$_3$) δ 7.51 (m, 4H), 7.43 (m, 6H), 5.06 (m, 2H), 3.01 (m, 4H), 2.61 (m, 4H); $^{13}$C NMR (100 MHz) (CDCl$_3$) δ 148.8, 142.5, 142.3, 128.9, 128.8, 128.5, 128.2, 126.4, 126.2, 126.0, 125.7, 109.9, 38.5, 38.3, 34.6.

Example 7. Preparation of (S)—N$^1$-(2-Phenethyl-4-phenylbutyl)pentane-1,2,5-triamine 3 TFA

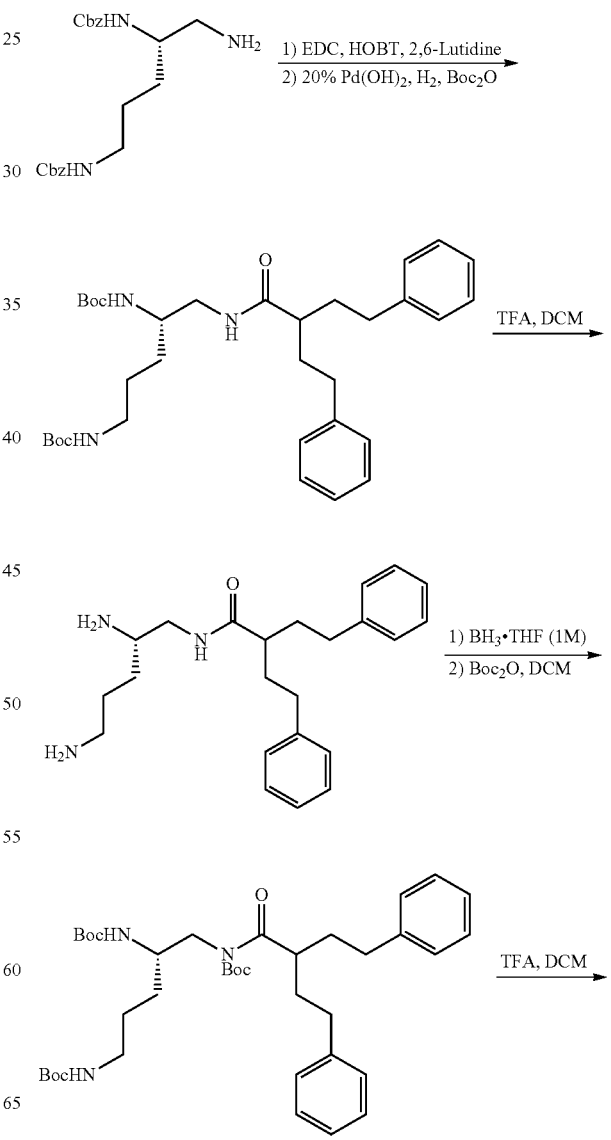

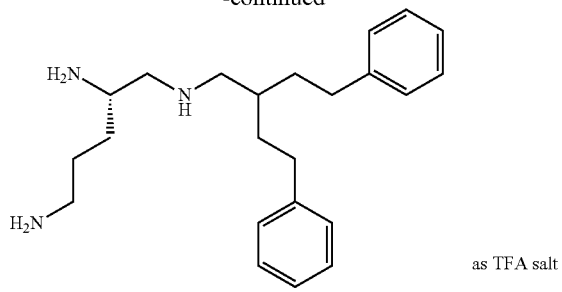

as TFA salt

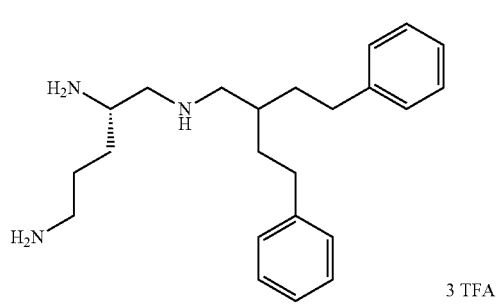 [SMILES: NCCC[C@H](N)CNCC(CCc1ccccc1)CCc1ccccc1]

3 TFA (S)—N¹-(2-phenethyl-4-phenylbutyl)pentane-1,2,5-triamine 3TFA

Di-tert-butyl (5-((tert-butoxycarbonyl)(2-phenethyl-4-phenylbutyl)amino)pentane-1,4-diyl)(S)-dicarbamate (22 mg, 0.034 mmol) was dissolved in DCM (1 mL) and TFA (0.5 mL) was added. Reaction mixture was stirred at room temperature for 2 hrs. On completion of the reaction, the solvents were removed on the rotary evaporated. Methanol was added and rotavapped three times to obtain product as a white solid. (21 mg, 100%); MP 140-142° C.; ¹H NMR (MeOD) (400 MHz) δ 7.12 (m, 10H), 3.59 (m, 1H), 3.25 (m, 1H), 3.03 (m, 2H), 2.87 (m, 2H), 2.55 (m, 4H), 1.68 (m, 10H); ¹³C NMR 142.9, 129.5, 129.4, 127.0, 54.0, 51.1, 39.9, 36.3, 33.9, 33.3, 29.4, 24.2;

The requisite intermediates were prepared as described in the following paragraphs.

Intermediate a

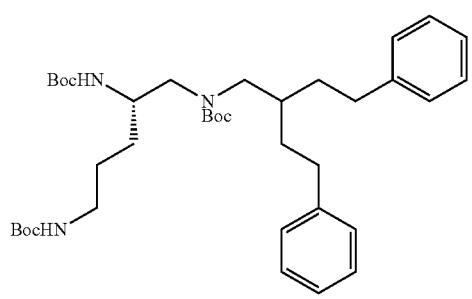 [SMILES: CC(C)(C)OC(=O)NCCC[C@@H](CN(CC(CCc1ccccc1)CCc1ccccc1)C(=O)OC(C)(C)C)NC(=O)OC(C)(C)C]

Di-tert-butyl (5-((tert-butoxycarbonyl)(2-phenethyl-4-phenylbutyl)amino)pentane-1,4-diyl)(S)-dicarbamate (S)—N-(2,5-Diaminopentyl)-2-phenethyl-4-phenylbutanamide (79 mg, 0.14 mmol) was dissolved in dry THF (10 mL) and BH₃.THF (2 mL) was added. The reaction mixture was stirred under reflux for overnight under nitrogen. Then methanol (10 mL) was added and the reaction was stirred at reflux for 2 hrs. On completion, 2 mL of water was added and reaction allowed to cool to room temperature. Then the reaction was dried with sodium sulfate and filtered. The organic layer was rotavapped to remove solvent. The residue was dissolved in DCM (5 mL) and Boc₂O (92 mg, 0.42 mmol) and reaction was stirred at room temperature for 2 hrs. The organic layer was rotavapped and residue purified on ISCO (0-30% EtOAc/Hexane) to give product as a colorless oil. (30 mg, 32%); ¹H NMR (400 MHz) (CDCl₃) δ 7.23 (m, 10H), 5.03 (brs, 1H), 4.65 (brs, 1H), 3.71 (m, 1H), 3.43 (m, 2H), 3.14 (m, 2H), 2.84 (m, 1H), 2.63 (m, 4H), 1.66 (m, 6H), 1.47 (s, 18H), 1.43 (s, 9H); ¹³C NMR (100 MHz) (CDCl₃) δ 155.5, 128.3, 125.8, 79.9, 79.0, 70.8, 62.7, 49.7, 49.4, 40.3, 35.9, 33.1, 33.0, 32.7, 30.7, 28.43, 28.4, 26.3

Intermediate b

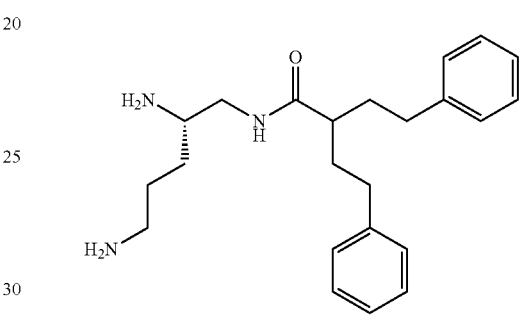

(S)—N-(2,5-Diaminopentyl)-2-phenethyl-4-phenylbutanamide

Di-tert-butyl (5-(2-phenethyl-4-phenylbutanamido)pentane-1,4-diyl)(S)-dicarbamate (80 mg, 0.14 mmol) was dissolved in DCM (5 mL) and TFA (2.5 mL) at 0° C. Reaction was stirred at that temperature for 2 hrs under nitrogen. The solvents were removed to obtain product as a TFA salt, colorless oil. (79 mg, 100%); ¹H NMR (400 MHz) (MeOD) δ 7.22 (m, 10H), 3.46 (m, 2H), 2.97 (m, 2H), 2.61 (m, 4H), 2.40 (m, 1H), 1.96 (m, 2H), 1.83 (m, 6H); ¹³C (100 MHz) (MeOD) δ 180.1, 143.0, 129.4, 129.3, 126.9, 52.7, 47.5, 42.0, 40.1, 35.6, 35.5, 34.7, 28.5, 24.4

Intermediate c

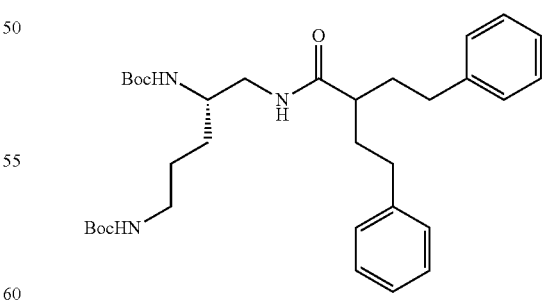

Di-tert-butyl (5-(2-phenethyl-4-phenylbutanamido)pentane-1,4-diyl)(S)-dicarbamate 2-Phenethyl-4-phenylbutanoic acid (158 mg, 0.59 mmol) was dissolved in DMF (5 mL) and EDC (227 mg, 1.19 mmol) and HOBT (166 mg, 1.19 mmol) were added. Reaction was stirred at room temperature for 5 minutes. Then dibenzyl (5-aminopentane-1,4-diyl)(S)-dicarbamate (200 mg, 0.54 mmol) was added followed by 2,6-lutidine (0.19 mL, 1.62 mmol). Reaction was stirred at room temperature overnight under nitrogen. The reaction mixture was then diluted with ethyl acetate, and washed with water, 1M HCl, saturated NaHCO$_3$, water and brine. The organic layer was dried over sodium sulfate and filtrate was concentrated to obtain a solid. This solid was dissolved in ethanol (15 mL), 20% Pd (OH)$_2$/C (80 mg) and BOC$_2$O (272 mg, 1.25 mmol) was added. The reaction mixture was stirred under hydrogen at room temperature overnight. On completion of the reaction, the mixture was filtered to remove catalyst and solvent rotavapped. The residue was purified on ISCO (0-10% Methanol/Dichloromethane) to get product as a white solid. (85 mg, 30%); $^1$H NMR (CDCl$_3$) (400 MHz) δ 7.22 (m, 10H), 6.33 (brs, 1H), 5.02 (brs, 1H), 4.80 (m, 1H); 3.70 (m, 1H). 3.35 (m, 2H), 3.14 (m, 2H), 2.59 (m, 4H), 2.14 (m, 1H), 2.02 (m, 2H), 1.78 (m, 2H), 1.57 (m, 4H), 1.45 (s, 9H), 1.39 (m, 9H)

Compound 8. Preparation of (S)—N5-(2-phenethyl-4-phenylbutyl)pentane-1,2,5-triamine 3 TFA

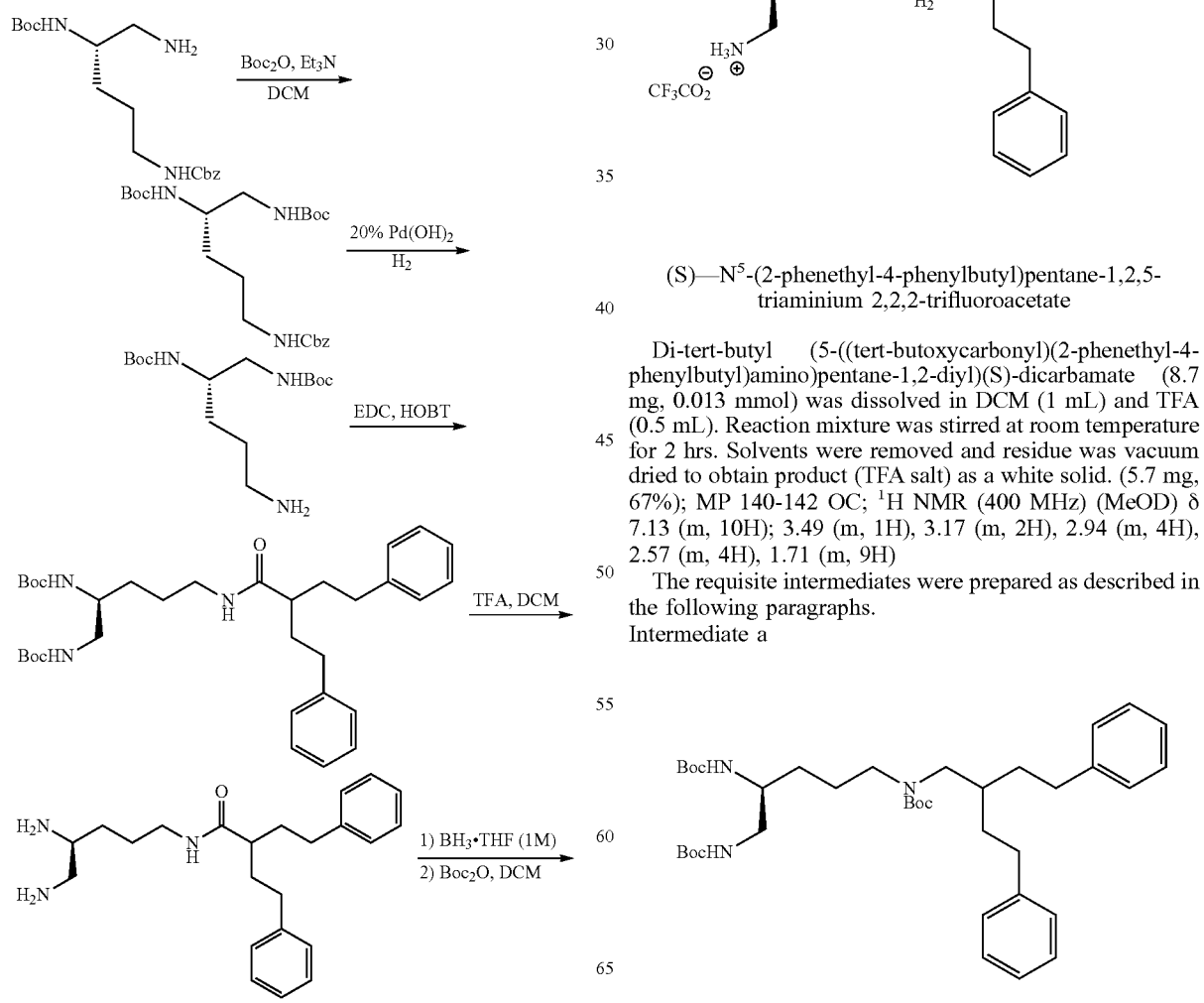

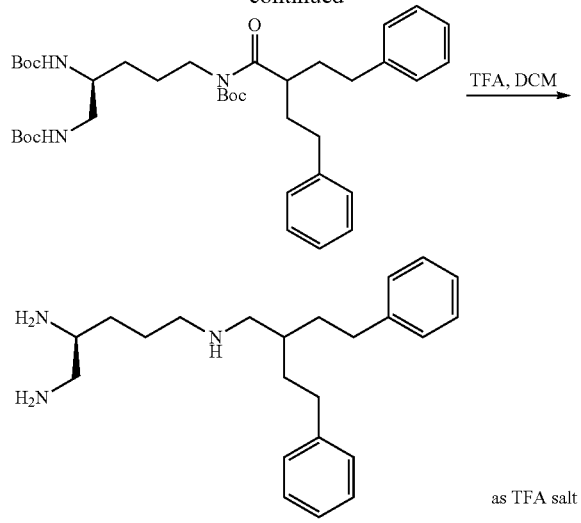

(S)—N$^5$-(2-phenethyl-4-phenylbutyl)pentane-1,2,5-triaminium 2,2,2-trifluoroacetate Di-tert-butyl (5-((tert-butoxycarbonyl)(2-phenethyl-4-phenylbutyl)amino)pentane-1,2-diyl)(S)-dicarbamate (8.7 mg, 0.013 mmol) was dissolved in DCM (1 mL) and TFA (0.5 mL). Reaction mixture was stirred at room temperature for 2 hrs. Solvents were removed and residue was vacuum dried to obtain product (TFA salt) as a white solid. (5.7 mg, 67%); MP 140-142 OC; $^1$H NMR (400 MHz) (MeOD) δ 7.13 (m, 10H); 3.49 (m, 1H), 3.17 (m, 2H), 2.94 (m, 4H), 2.57 (m, 4H), 1.71 (m, 9H)

The requisite intermediates were prepared as described in the following paragraphs.

Intermediate a

Di-tert-butyl (5-((tert-butoxycarbonyl)(2-phenethyl-4-phenylbutyl)amino)pentane-1,2-diyl)(S)-dicarbamate (S)—N-(4,5-Diaminopentyl)-2-phenethyl-4-phenylbutanamide (80 mg, 0.14 mmol) was dissolved in 10 mL of THF and BH$_3$.THF (2 mL) and the mixture was heated at 83° C. for overnight. Then methanol (10 mL) was added and the reaction mixture was stirred at that same temperature for 2 hours. Then water (1 mL) was added and the reaction cooled to room temperature. Solvents presents were then rotavapped and redissolved in DCM, dried with sodium sulfate and organic layer filtered and solvent removed to give an oil residue. The residue was redissolved in DCM and Boc$_2$O was added and reaction stirred for 2 hrs. Workup was done by phase extraction with water and ethyl acetate. The organic layer was dried over sodium sulfate and filtered and rotavapped. The residue was purified on ISCO (0-30% Ethyl acetate/Hexane) to give product as a colorless oil (9 mg, 10%); $^1$H NMR (400 MHz) (MeOD) δ 7.24 (m, 10H), 4.72 (m, 2H), 3.62 (brs, 1H), 3.17 (m, 6H), 2.67 (m, 4H), 1.78 (m, 1H), 1.66 (m, 8H), 1.46 (m, 27H).
Intermediate b

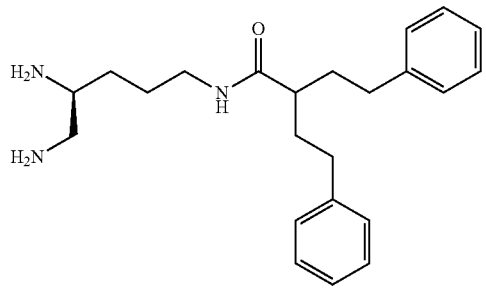 [SMILES: NC[C@@H](N)CCCNC(=O)C(CCc1ccccc1)CCc1ccccc1]

(S)—N-(4,5-Diaminopentyl)-2-phenethyl-4-phenylbutanamide

Di-tert-butyl (5-(2-phenethyl-4-phenylbutanamido)pentane-1,2-diyl)(S)-dicarbamate (80 mg, 0.14 mmol) was dissolved in DCM (1 mL) and TFA (0.5 mL) and the reaction mixture was stirred at 0° C. for 2 hrs. Then the solvents were rotavapped and vacuum dried to obtained product as a colorless oil. (80 mg, 100%); $^1$H NMR (400 MHz) (MeOD) δ 7.10 (m, 10H), 3.52 (m, 1H), 3.18 (m, 4H), 2.47 (m, 4H), 2.20 (m, 1H), 1.83 (m, 2H), 1.69 (m, 6H); $^{13}$C NMR (100 MHz) (MeOD) δ 178.7, 143.1, 129.4, 129.3, 126.9, 50.5, 47.6, 42.2, 39.6, 35.8, 34.8, 29.2, 26.2
Intermediate c

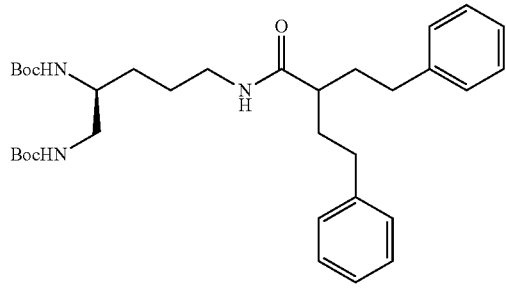 [SMILES: CC(C)(C)OC(=O)NC[C@H](CCCNC(=O)C(CCc1ccccc1)CCc1ccccc1)NC(=O)OC(C)(C)C]

Di-tert-butyl (5-(2-phenethyl-4-phenylbutanamido)pentane-1,2-diyl)(S)-dicarbamate 2-Phenethyl-4-phenylbutanoic acid was dissolved in DMF (5 mL) and EDC (185 mg, 0.96 mmol) and HOBT (185 mg, 0.96 mmol) were added. Reaction was stirred at room temperature for 5 minutes. Then di-tert-butyl (5-aminopentane-1,2-diyl)(S)-dicarbamate (140 mg, 0.44 mmol) was added followed by 2,6-lutidine (0.15 mL, 1.32 mmol). Reaction was stirred at room temperature overnight under nitrogen. The reaction mixture was then diluted with ethyl acetate, and washed with water, 1M HCl, saturated NaHCO$_3$, water and brine. The organic layer was dried over sodium sulfate and filtrate was concentrated and purified on ISCO (0-10% Methanol/dichloromethane) to obtain a solid. (85 mg, 34%); $^1$H NMR (CDCl$_3$) (400 MHz) δ 7.23 (m, 10H), 5.96 (brs, 1H), 4.97 (brs, 2H), 3.66 (m, 1H), 3.38 (m, 1H), 3.24 (m, 3H), 2.59 (m, 4H), 2.04 (m, 3H), 1.78 (m, 2H), 1.69 (m, 4H), 1.45 (s, 9H), 1.44 (s, 9H); $^{13}$C NMR (CDCl$_3$) (100 MHz) δ 175.2, 156.7, 156.3, 141.7, 128.4, 128.3, 125.9, 79.4, 51.2, 46.5, 44.4, 39.0, 34.3, 33.6, 30.4, 28.3, 25.9.
Intermediate d

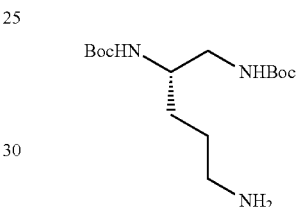

Di-tert-butyl (5-aminopentane-1,2-diyl)(S)-dicarbamate

Benzyl di-tert-butyl pentane-1,2,5-triyl(S)-tricarbamate (200 mg, 0.44 mmol) was dissolved in ethanol (10 mL) and 20% Pd(OH)$_2$/C (40 mg) and stirred under hydrogen atmosphere overnight. Then the catalyst was filtered off and filtrate concentrated to give product as an oil (140 mg, 100%); $^1$H NMR (400 MHz) (CDCl$_3$) δ 5.22 (brs, 1H), 5.13 (brs, 1H), 4.53 (m, 2H), 3.54 (m, 1H), 3.10 (m, 2H), 2.76 (m, 2H), 1.54 (m, 2H), 1.36 (s, 18H); $^{13}$C NMR (100 MHz) (CDCl$_3$) δ 156.7, 156.4, 128.4, 127.9, 79.22, 51.1, 44.5, 40.8, 29.9, 28.3, 27.3
Intermediate e

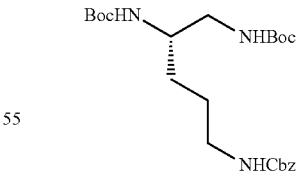

Benzyl di-tert-butyl pentane-1,2,5-triyl(S)-tricarbamate

Benzyl tert-butyl (5-aminopentane-1,4-diyl)(S)-dicarbamate (332 mg, 0.95 mmol) was dissolved in DCM (5 mL) and triethyl amine (0.20 mL, 1.42 mmol) was added. Then Boc$_2$O was added and the reaction was stirred at room temperature overnight. The reaction mixture was then washed with water and the organic layer separated. The organic layer was dried with sodium sulfate, concentrated and purified on ISCO (0-50% EtOAc/Hexane) to give product as a yellow colored solid (252 mg, 56%); $^1$H NMR (400 MHz) (CDCl$_3$) δ 7.33 (m, 5H), 5.13 (brs, 1H), 5.09 (s, 2H), 4.98 (s, 1H), 4.83 (brs, 1H), 3.61 (s, 1H), 3.18 (m, 4H), 1.52 (m, 4H), 1.38 (s, 18H); $^{13}$C NMR (100 MHz) (CDCl$_3$) δ 156.5, 156.1, 136.6, 128.4, 128.1, 128.0, 79.3, 66.5, 51.1, 44.4, 40.7, 29.9, 28.3, 26.2.

Example 9. Preparation of (2S,E)-6-methyl-N1-(2-phenethyl-4-phenylbutylidene)heptane-1,2,5-triaminium chloride

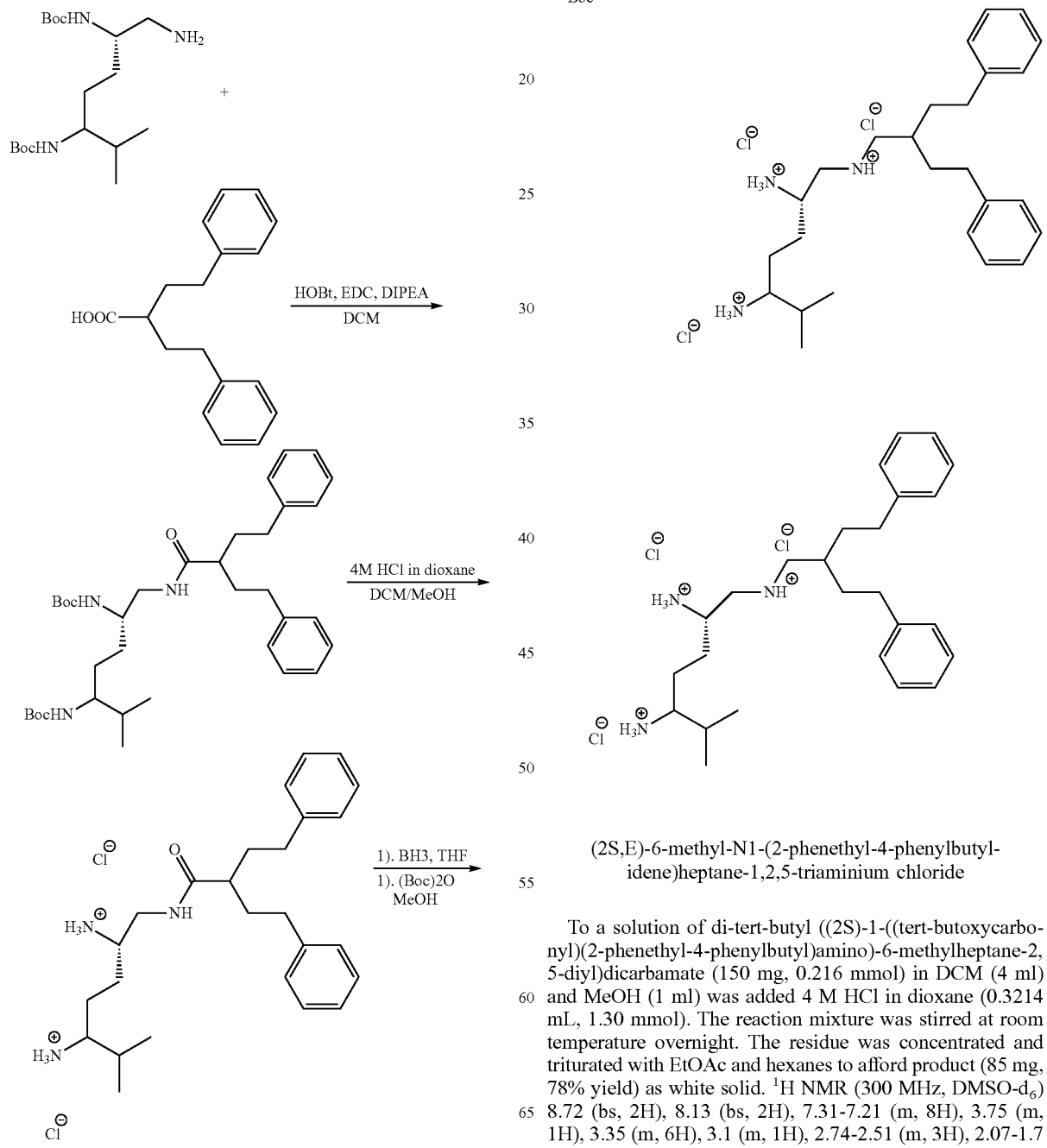

(2S,E)-6-methyl-N1-(2-phenethyl-4-phenylbutylidene)heptane-1,2,5-triaminium chloride To a solution of di-tert-butyl ((2S)-1-((tert-butoxycarbonyl)(2-phenethyl-4-phenylbutyl)amino)-6-methylheptane-2,5-diyl)dicarbamate (150 mg, 0.216 mmol) in DCM (4 ml) and MeOH (1 ml) was added 4 M HCl in dioxane (0.3214 mL, 1.30 mmol). The reaction mixture was stirred at room temperature overnight. The residue was concentrated and triturated with EtOAc and hexanes to afford product (85 mg, 78% yield) as white solid. $^1$H NMR (300 MHz, DMSO-d$_6$) 8.72 (bs, 2H), 8.13 (bs, 2H), 7.31-7.21 (m, 8H), 3.75 (m, 1H), 3.35 (m, 6H), 3.1 (m, 1H), 2.74-2.51 (m, 3H), 2.07-1.7 (m, 6H), 0.95 (m, 6H).

The requisite intermediates were prepared as described in the following paragraphs.

Intermediate a

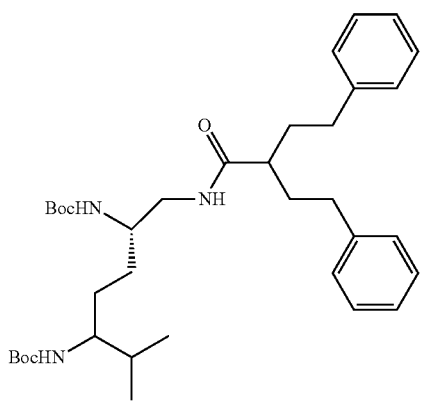 [SMILES: CC(C)C(CC[C@@H](CNC(=O)C(CCc1ccccc1)CCc1ccccc1)NC(=O)OC(C)(C)C)NC(=O)OC(C)(C)C]

di-tert-butyl ((2S)-6-methyl-1-(2-phenethyl-4-phenylbutanamido)pentane-2,5-diyl) dicarbamate To 2-phenethyl-4-phenylbutanoic acid (269 mg, 1.00 mmol) in dry DCM (10 mL) was added DIPEA (0.435 mL, 1.0 mmol), HOBt (68 mg, 0.50 mmol), EDC (190 mg, 1.0 mmol). The reaction mixture was stirred at room temperature for 5 minutes. di-tert-butyl ((2S)-1-amino-6-methylheptane-2,5-diyl)dicarbamate (300 mg, 0.834 mmol) was added and the reaction was continued at room temperature overnight. The reaction mixture was then diluted with DCM and washed with saturated NaHCO$_3$ and brine. The organic layer was dried over sodium sulfate and filtered. Filtrate was then concentrated and purified using an ISCO chromatograph with silica (0-100% ethyl acetate/hexanes) to give the product (342 mg, 81% yield) as a white solid. $^1$H NMR (CDCl$_3$) (300 MHz) δ 7.31-7.16 (m, 10H), 3.35 (m, 3H), 2.62 (m, 4H), 2.1 (m, 2H), 1.7 (m, 4H), 1.40 (m, 22H), 0.91 (m, 6H).

Intermediate b

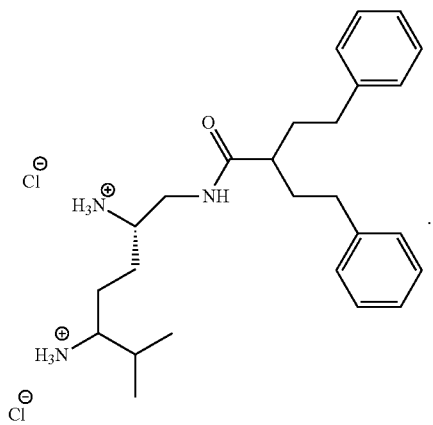 [SMILES: [Cl-] ; CC(C)C([NH3+])CC[C@H]([NH3+])CNC(=O)C(CCc1ccccc1)CCc1ccccc1 ; [Cl-]]

N-(((2S)-6-methyl-1-(2-phenethyl-4-phenylbutanamido)heptane-2,5-diaminium chloride To a solution of di-tert-butyl ((2S)-6-methyl-1-(2-phenethyl-4-phenylbutanamido)heptane-2,5-diyl)dicarbamate (320 mg, 0.525 mmol) in DCM (4 ml) and MeOH (1 ml) was added 0.656 ml HCl in dioxane. The reaction mixture was stirred at room temperature overnight. The residue was concentrated and triturated with EtOAc and hexanes to afford product (210 mg, 83% yield) as white solid. $^1$H NMR (300 MHz, DMSO-d$_6$) δ 8.5 (m, 1H), 8.28 (m, 2H), 8.07 (m, 2H), 7.30-7.17 (m, 7H), 3.35 (m, 3H), 3.2 (m, 1H), 2.9 (m, 1H), 2.51 (m, 4H), 2.4 (m, 1H), 1.99-1.68 (m, 6H), 1.18 (m, 2H), 0.91 (m, 6H).

Intermediate c

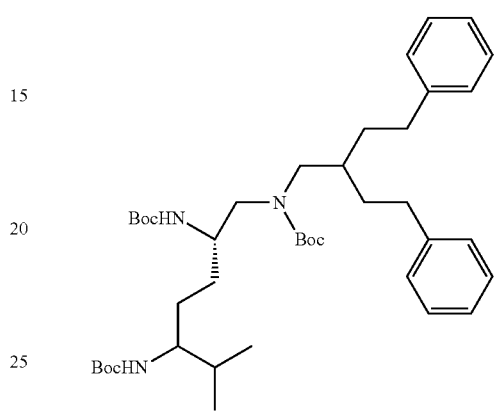

di-tert-butyl ((2S)-1-((tert-butoxycarbonyl)(2-phenethyl-4-phenylbutyl)amino)-6-methylheptane-2,5-diyl)dicarbamate To the solution of (2S)-6-methyl-1-(2-phenethyl-4-phenylbutanamido)heptane-2,5-diaminium chloride (150 mg, 0.310 mmol) in THF (20 mL) was added 1M BH3 in THF (2 ml), the reaction mixture was refluxed overnight. After the reaction was cooled down to room temperature, it was quenched with 2 ml MeOH and 0.5 ml water. The resulting mixture was refluxed again for 1 hour. The reaction was concentrated and added 10 ml MeOH and 200 mg (Boc)$_2$O, stirred at room temperature for 2 hours. After the reaction was concentrated, it was diluted with EtOAc, washed with saturated NaHCO$_3$ and brine. The organic layer was dried over sodium sulfate and filtered. Filtrate was then concentrated and purified using an ISCO chromatograph with silica (0-70% ethyl acetate/hexanes) to give the product (155 mg, 72% yield) as a white solid. $^1$H NMR (CDCl$_3$) (300 MHz) δ 7.29-7.16 (m, 10H), 3.8 (m, 1H), 3.45 (m, 2H), 3.2 (m, 2H), 2.68 (m, 5H), 1.64-1.28 (m, 36H), 0.92 (m, 6H).

Example 10. Preparation of (2S)—N$^1$-(1,5-diphenylpentan-3-yl)-6-methylheptane-1,2,5-triaminium chloride

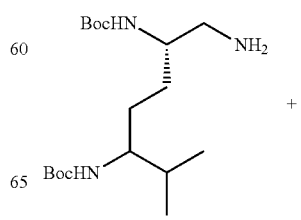

+

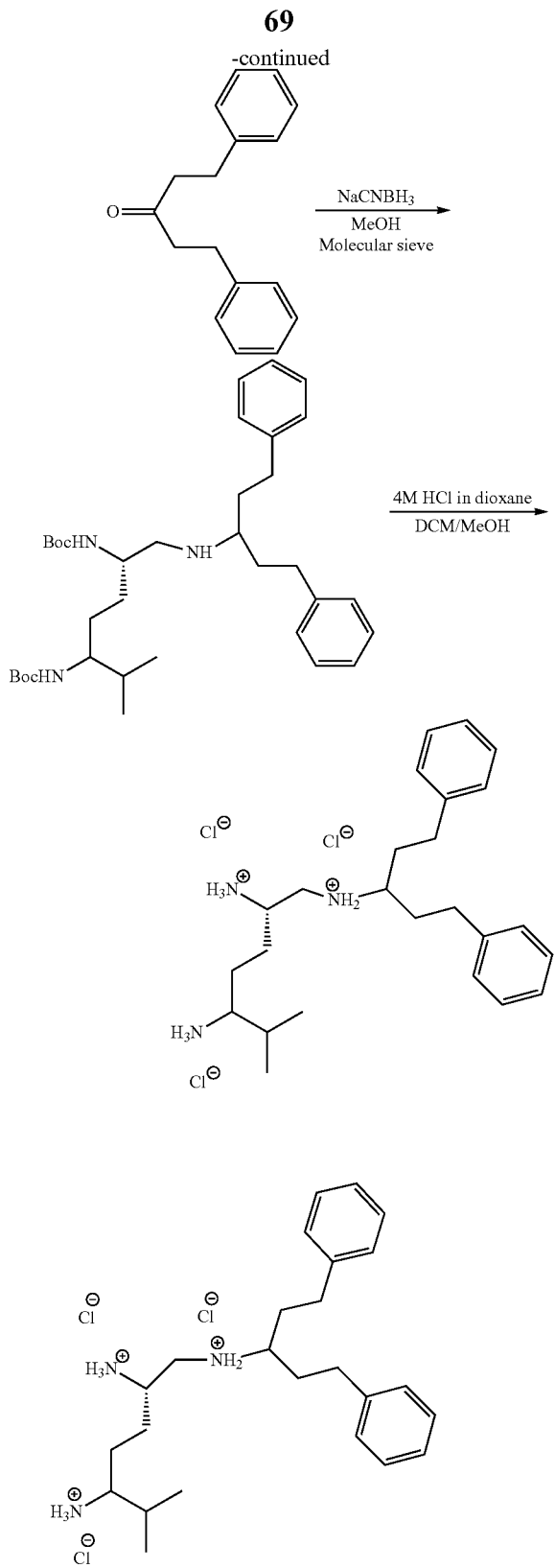

(2S)—N[1]-(1,5-diphenylpentan-3-yl)-6-methylheptane-1,2,5-triaminium chloride

To a solution of (S)-di-tert-butyl (5-((3,5-bis(trifluoromethyl)benzyl)amino)pentane-1,4-diyl) dicarbamate (110 mg, 0.278 mmol) in DCM (4 ml) and MeOH (1 ml) was added 0.4 ml HCl in dioxane. The reaction was stirred at room temperature overnight. The residue was concentrated and triturated with EtOAc and hexanes to afford product (83 mg, 89% yield) as white solid. $^1$H NMR (300 MHz, DMSO-$d_6$) δ 8.72 (bs, 2H), 8.13 (bs, 2H), 7.24 (m, 8H), 3.75 (m, 1H), 3.35 (m, 6H), 3.1 (m, 1H), 2.75 (m, 3H), 2.1-1.7 (m, 6H), 0.95 (m, 6H).

The requisite intermediate was prepared as described in the following paragraph.

Intermediate a

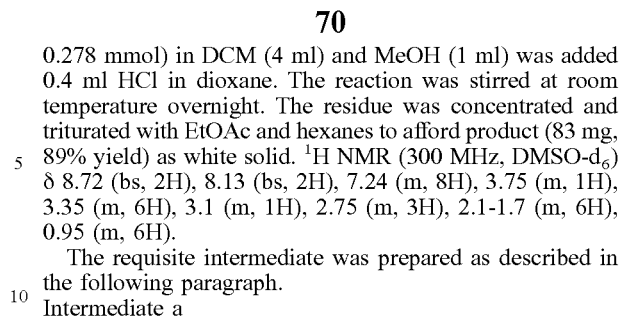

(S)-di-tert-butyl (5-((3,5-bis(trifluoromethyl)benzyl)amino)pentane-1,4-diyl) dicarbamate To a solution of di-tert-butyl ((2S)-1-amino-6-methylheptane-2,5-diyl)dicarbamate (100 mg, 0.278 mmol) and 1,5-diphenylpentan-3-one (79.5 mg, 0.334 mmol) in MeOH (10 ml) was added molecular sieve and sodium cyanoborohydride (52.4 mg, 0.834 mmol). The reaction was stirred at room temperature overnight. The molecular sieve was filtered off and washed with EtOAc. The filtration was concentrated and partitioned between EtOAc and sat. NaHCO$_3$ solution, extracted with EtOAc (3×10 mL), the organic layers was washed with brine, concentrated. The residue was purified on ISCO (0-100% ethyl acetate/Hexane) to give product (112 mg, 69% yield) as a semi-solid. $^1$H NMR (300 MHz, DMSO-$d_6$) δ 7.33-7.16 (m, 10H), 3.75 (m, 1H), 3.4 (m, 2H), 2.68 (m, 6H), 1.85 (m, 4H), 1.30 (m, 23H), 0.92 (m, 6H).

Example 11. Preparation of 3-((1,5-diphenylpentan-3-yl)oxy)propane-1,2-diamine

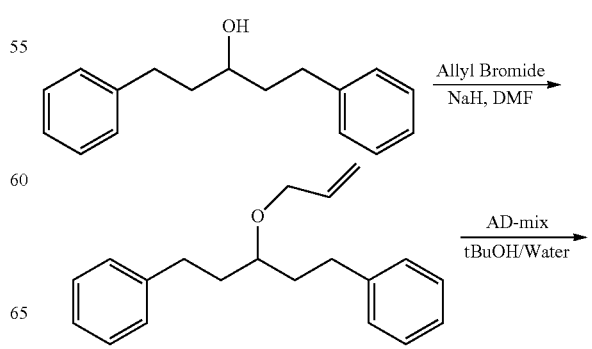

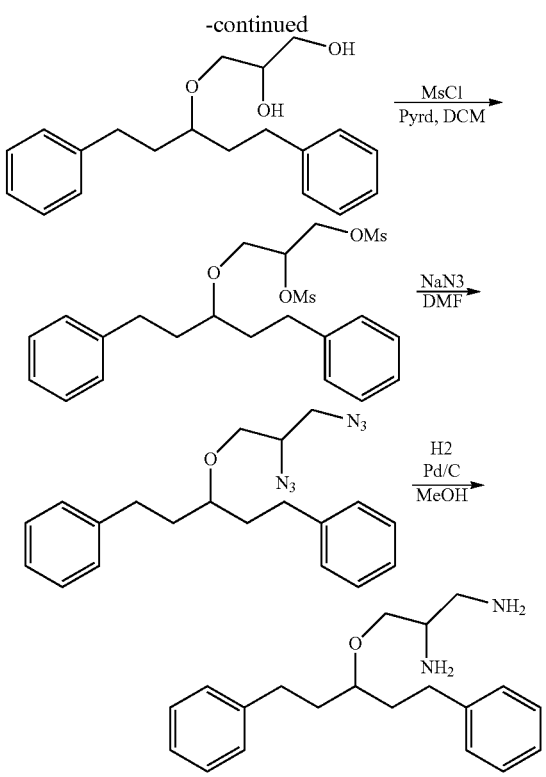

3-((1,5-diphenylpentan-3-yl)oxy)propane-1,2-diamine

The mixture of (3-(2,3-diazidopropoxy)pentane-1,5-diyl)dibenzene (300 mg, xx mmol) in MeOH (10 mL), Pd/C (60 mg) was subjected hydrogenation with H₂ balloon for 16 hours. The reaction mixture was filtered from catalyst, the filtrate was concentrated to give the product as an oil (0.25 g, 95% yield). 1H NMR (CDCl₃) (300 MHz) δ 7.31-7.17 (m, 10H), 3.52-3.26 (m, 6H), 2.81 (m, 4H), 1.81 (m, 4H).

The requisite intermediates were prepared as described in the following paragraphs.

Intermediate a

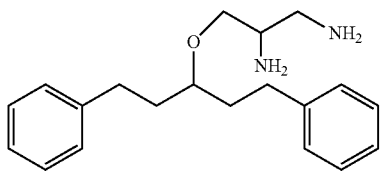 [SMILES: NCC(N)COC(CCc1ccccc1)CCc1ccccc1]

(3-(allyloxy)pentane-1,5-diyl)dibenzene

To a solution of 3-((1,5-diphenylpentan-3-yl)oxy)propane-1,2-diol (225 mg, 1.0 mmol) in DMF (5 mL) was added NaH (60% in mineral oil, 80 mg, 2.0 mmol) in several portions over 10 min. The mixture was stirred at room temperature for 30 minutes after which allyl bromide (0.35 mL, 4.0 mmol) was added. The reaction was continued to stir at room temperature for 1 h. The reaction mixture was diluted with ethyl acetate and was washed with 1 N HCl, 15% LiCl and brine. Drying with sodium sulfate followed by concentration afforded the crude product which was purified by ISCO to give product as oil (224 mg, 80% yield). 1H NMR (CDCl₃) (300 MHz) δ 7.31-7.17 (m, 10H), 5.97 (m, 1H), 5.32-5.16 (m, 2H), 4.00 (m, 2H), 3.39-3.35 (m, 1H), 2.75-2.6 (m, 4H), 1.93-1.81 (m, 4H).

Intermediate b

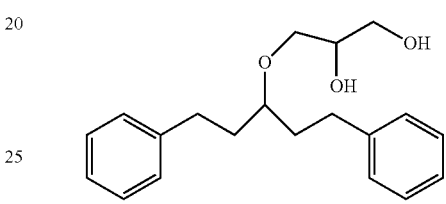

3-((1,5-diphenylpentanyl)oxy)propane-1,2-diol (3-(Allyloxy)pentane-1,5-diyl))dibenzene (224 mg, 0.8 mmol) was added in one portion to a stirred solution of ADmix-β (1.12 g) in 1:1 tert-butyl alcohol-water (10 ml) at 0° C. The resulting orange slurry was stirred vigorously at room temperature for 24 h. Sodium sulfite (1.4 g) was then added and the mixture allowed to warm to room temperature. After stirring at room temperature for 1 h, CH₂Cl₂ (20 ml) was added and the layers separated. The aqueous layer was extracted with CH₂Cl₂ (5×20 ml). The combined organic extracts were dried (Na₂SO₄) and evaporated under reduced pressure to give the crude product as an oil. Purification by chromatography on silica with EtOAc as eluant gave the diol (265 mg, 84% yield). 1H NMR (CDCl₃) (300 MHz) δ 7.31-7.16 (m, 10H), 3.83 (m, 1H), 3.72-3.65 (m, 2H), 3.53 (m, 2H), 3.37 (m, 1H), 2.71-2.64 (m, 4H), 1.91-1.83 (m, 4H).

Intermediate c

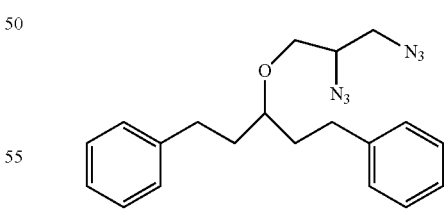

(3-(2,3-diazidopropoxy)pentane-1,5-diyl)dibenzene

To a solution of 3-((1,5-diphenylpentane-3-yl)oxy)propane-1,2-diol (260 mg, 0.82 mmol) in dry DCM (5 mL) was added pyridine (0.4 mL) and MsCl (0.46 ml) at 0° C. with stirring. Stirring was continued for 12 h at room temperature then the reaction was quenched by adding saturated aqueous NaHCO₃. The DCM phase was separated and concentrated to give the crude dimesylate. A mixture of the crude dimesylate (325 mg, 0.69 mmol and NaN3 (180 mg, 2.76 mmol) in DMF (5 mL) was heated at 800° C. for 2 h. The resulting mixture was distributed between hexane and water. The hexane phase was separated and dried over anhydrous Na2SO4 and solvents removed under reduced pressure to give the diazide (300 mg, 99% yield). 1H NMR (CDCl3) (300 MHz) δ δ 7.32-7.17 (m, 10H), 3.73 (m, 1H), 3.53 (m, 2H), 3.46-3.36 (m, 3H), 2.73 (m, 4H), 1.90 (m, 4H).

Example 12. Preparation of 3-(2-phenyethyl-4-phenylbutoxy)propane-1,2-diamine

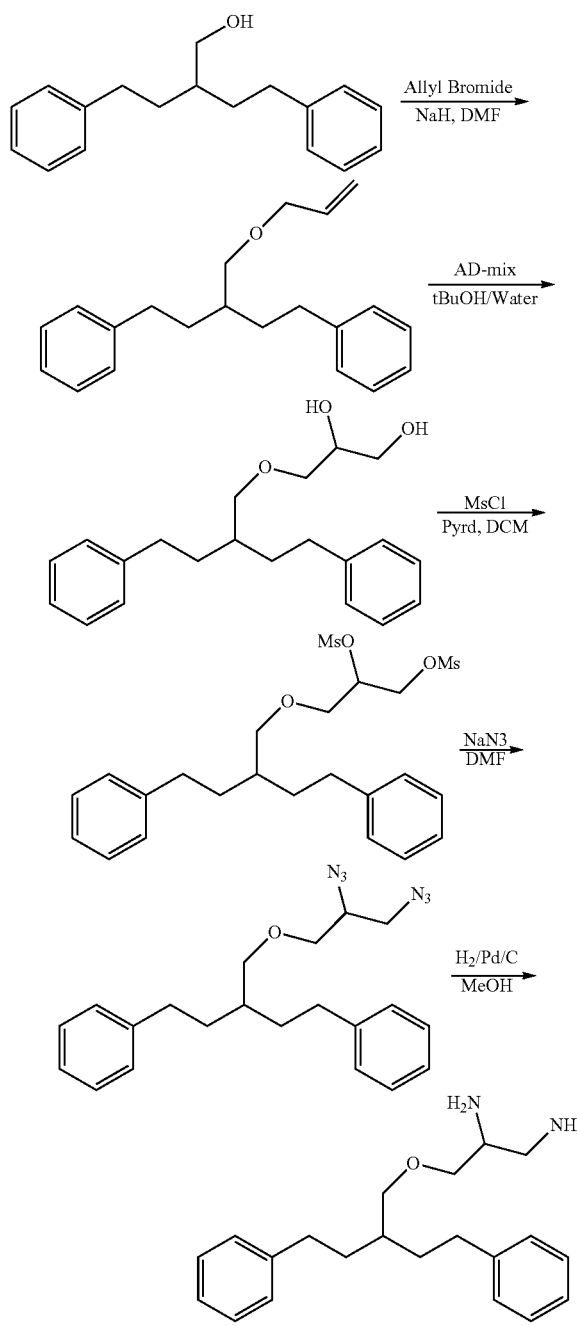

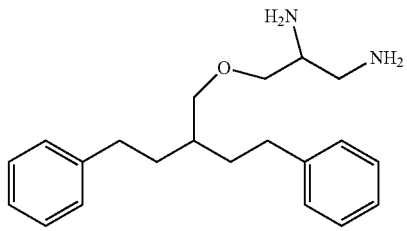 [SMILES: NCC(N)COCC(CCc1ccccc1)CCc1ccccc1]

3-(2-phenethyl-4-phenylbutoxy)propane-1,2-diamine

The mixture of (3-(2,3-diazidopropoxy)pentane-1,5-diyl) dibenzene (80 mg, 0.21 mmol) in MeOH (3 mL), Pd/C (20 mg) was subjected hydrogenation with H2 balloon for 16 hours. The reaction mixture was filtered from catalyst, the filtrate was concentrated to give the product as a clear oil (65 mg, 94% yield). 1H NMR (CDCl3) (300 MHz) δ 7.30-7.17 (m, 10H), 3.42-3.36 (m, 3H), 3.28 (m, 1H), 2.91 (m, 1H), 2.80 (m, 1H), 2.75-2.55 (m, 5H), 1.71 (m, 4H).

The requisite intermediate was prepared as described in the following paragraphs.

Intermediate a

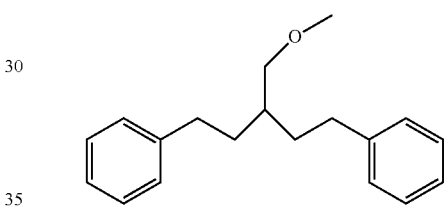

(3-((allyloxy)methyl)pentane-1,5-diyl)dibenzene

To a solution of 2-phenethyl-4-phenylbutane-1-ol (540 mg, 2.13 mmol) in DMF (10 mL) was added NaH (60% in mineral oil, 135 mg, 3.2 mmol) in several portions over 10 min. The mixture was stirred at room temperature for 30 minutes after which allyl bromide (0.56 mL, 6.4 mmol) was added. The reaction was continued to stir at room temperature for 1 h. The reaction mixture was diluted with ethyl acetate and was washed with 1 N HCl, 15% LiCl and brine. Drying with sodium sulfate followed by concentration afforded the crude product which was purified by ISCO to give product as colorless oil (595 mg, 95% yield). 1H NMR (CDCl3) (300 MHz) δ 7.32-7.16 (m, 10H), 5.98-5.85 (m, 1H), 5.31-5.16 (m, 2H), 3.96 (m, 2H), 3.42 (m, 2H), 2.61 (m, 4H), 1.68 (m, 4H).

Intermediate b

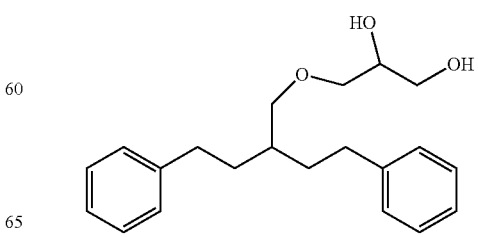

3-(2-phenethyl-4-phenylbutoxy)propane-1,2-diol (3-((Allyloxy)methyl)pentane-1,5-diyl)dibenzene (294 mg, 1.0 mmol) was added in one portion to a stirred solution of ADmix-β (1.4 g) in 1:1 tert-butyl alcohol-water (20 ml) at 0° C. The resulting orange slurry was stirred vigorously at room temperature for 24 h. Sodium sulfite (1.4 g) was added. After stirring at room temperature for 1 h, $CH_2Cl_2$ (20 ml) was added and the layers separated. The aqueous layer was extracted with $CH_2Cl_2$ (5×20 ml). The combined organic extracts were dried ($Na_2SO_4$) and evaporated under reduced pressure to give the crude product as an oil. Purification by chromatography on silica with EtOAc as eluant gave the diol (241 mg, 73% yield). 1H NMR ($CDCl_3$) (300 MHz) δ 7.29-7.15 (m, 10H), 3.85 (m, 1H), 3.7 (m, 2H), 3.5-3.54 (m, 4H), 2.63 (m, 4H), 1.7 (m, 4H).

Intermediate c

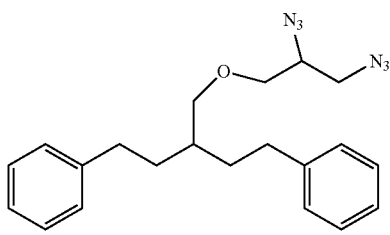 [SMILES: [N-]=[N+]=NCC(COCC(CCc1ccccc1)CCc1ccccc1)N=[N+]=[N-]]

(3-((2,3-diazidopropoxy)methyl)pentane-1,5-diyl) dibenzene

To a solution of diol 3-(2-phenethyl-4-phenylbutoxy) propane-1,2-diol (130 mg, 0.4 mmol) in dry DCM (2.0 mL) was added pyridine (0.1 ml, 1.2 mmol) and MsCl (0.1 ml, 1.2 mmol) at 0° C. with stirring. Stirring was continued for 12 h at room temperature then the reaction was quenched by adding saturated aqueous $NaHCO_3$. The DCM phase was separated and concentrated to give the crude dimesylate. A mixture of the crude dimesylate and NaN3 (90 mg, 1.4 mmol) in DMF (2 mL) was heated at 800° C. for 2 h. The resulting mixture was distributed between hexane and water. The hexane phase was separated and dried over anhydrous Na2SO4 and solvents removed under reduced pressure to give the diazide (120 mg, 80% yield). 1H NMR ($CDCl_3$) (300 MHz) δ 7.31-7.16 (m, 10H), 3.63 (m, 1H), 3.53 (m, 2H), 3.46-3.36 (m, 4H), 2.63 (m, 4H), 1.70 (m, 4H).

Example 13. Description of Test Methods

Test A. Minimum Inhibitory Concentration (MIC)-Based Assay for Potentiation of Antibiotics that are Known Efflux Pump Substrates:

MIC-based assays were used to evaluate the impact of potential efflux pump inhibiting (EPI) compounds on the MICs of antibiotics (e.g., clarithromycin and levofloxacin) known to be substrates for Gram-negative bacterial efflux pumps. The assays were conducted in accordance with Clinical and Laboratory Standards Institute (CLSI) guidelines for broth microdilution, with the modification that assays were conducted in the presence and absence of the test EPI compounds. When present, the EPI compounds were added to cation-adjusted Mueller-Hinton (CAMH) broth (Becton, Dickinson and Co., Franklin Lakes, N.J.) at a final concentration in the range of 1.6 to 12.5 μg/mL.

Log-phase Gram-negative bacteria were added to 96-well microtiter plates (at $5\times10^5$ colony forming units (CFU) per mL) containing two-fold serial dilutions of antibiotic in CAMH broth either in the absence or presence of the test EPI compounds. In all assays, each serial dilution of antibiotic was present in duplicate. The final volume in each well was 0.1 mL, and the microtiter plates were incubated aerobically for 24 hours at 37° C. Bacterial growth was then monitored by measuring the optical density (OD) at 600 nm using a VersaMax® plate reader (Molecular Devices, Inc., Sunnyvale, Calif.), with the MIC being defined as the lowest compound concentration at which growth was ≥90% inhibited compared to antibiotic-free control. The following Gram-negative bacterial strains were included in these assays:

*Escherichia coli* ATCC 25922

*Klebsiella pneumoniae* ATCC 13883 and ATCC 10031

*Pseudomonas aeruginosa* ATCC 27853.

Test B. Fluorescence-Based Cellular Assay for Efflux Inhibition:

The impact of potential EPI compounds on the activity of efflux pumps was also evaluated with a fluorescence-based cellular assay that measures the efflux of Hoechst 33342, a known substrate of Gram-negative bacterial efflux pumps. When bound to intracellular bacterial DNA, Hoechst 33342 fluoresces brightly, while the unbound fluorophore outside the bacterial cell exhibits little or no fluorescence. Thus, the efflux of Hoechst 33342 from inside to outside the bacterial cell is associated with a substantive decrease in fluorescence.

Bacterial cells were harvested from overnight cultures by centrifugation, and the cell pellet was washed with phosphate-buffered containing 1 mM $MgCl_2$ (PBSM). After washing the cells, the cell pellets were resuspended in PBSM to achieve a final OD at 600 nm of 0.6 to 0.9. The ATP required for efflux pump function was then depleted by addition of carbonyl cyanide 3-chlorophenylhydrazone (CCCP) to a final concentration in the range of 3 to 10 μM. Hoechst 33342 was then added to a final concentration of 10 μM, and the cells were incubated aerobically at 37° C. for 0.5 to 18 hours. The bacterial suspension (200 μL) was added to wells of a black, flat-bottom 96-well plate containing test EPI compounds at concentrations of ranging from 1.6 to 25 μg/mL or an equivalent volume of the vehicle (DMSO) alone. A plate vortexer was used to mix the bacterial cells with the test EPI compounds, and the plates are pre-incubated at 37° C. for 5 minutes. After the pre-incubation, Hoechst 33342 efflux was initiated by addition of glucose to a final concentration of 10 to 50 mM. A SpectraMax® 2 fluorescent plate reader (Molecular Devices, Inc., Sunnyvale, Calif.) was used to monitor the fluorescence of each well at 37° C. once per minute for 20 to 60 minutes. The excitation and emission wavelengths were set at 355 and 460 nm, respectively. *E. coli* ATCC 25922, *K. pneumoniae* ATCC 13883, and *P. aeruginosa* ATCC 27853 were used as model Gram-negative bacterial strains in this assay.

Example 14

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

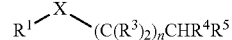

X is $NR^2$ or O;
$R^1$ is $(C_3-C_{12})$alkyl substituted with two or more groups selected
from $-NR^{b1}R^{c1}$, $-NHNH_2$, $-C(=NR^{a1})(NR^{b1}R^{c1})$, $-NR^{a1}C(=NR^{a1})(R^{d1})$
and $-NR^{a1}C(=NR^{a1})(NR^{b1}R^{c1})$;
$R^2$ is hydrogen or $(C_1-C_3)$alkyl;
each $R^3$ is independently hydrogen, halo or $(C_1-C_4)$alkyl;
$R^4$ is aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^5$ is hydrogen, $(C_1-C_3)$alkyl, aryl, heteroaryl, aryl$(C_1-C_6)$alkyl- or heteroaryl$(C_1-C_6)$alkyl- wherein any aryl, heteroaryl, aryl$(C_1-C_6)$alkyl- or heteroaryl$(C_1-C_6)$alkyl- of $R^5$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy, provided that when $R^5$ is hydrogen or $(C_1-C_3)$alkyl, and $R^4$ is optionally substituted phenyl, then n is not 0 or 1;
each $R^{a1}$ is independently hydrogen or $(C_1-C_4)$alkyl;
each $R^{b1}$ and $R^{c1}$ is independently hydrogen or $(C_1-C_4)$alkyl;
$R^{d1}$ is $(C_1-C_3)$alkyl and
n is 0, 1, 2 or 3;
or a salt thereof.

2. The compound of claim 1, which is a compound of formula Ia:

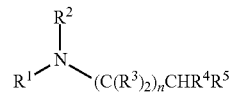

or a salt thereof.

3. The compound of claim 1, wherein $R^2$ is hydrogen.

4. The compound of claim 1 which is a compound of formula Ib:

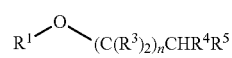

or a salt thereof.

5. The compound of any one of claim 1, wherein each $R^3$ is hydrogen.

6. The compound of claim 1, wherein n is 0 or 1.

7. The compound of claim 1, wherein $R^4$ is aryl or aryl$(C_1-C_6)$alkyl- wherein any aryl or aryl$(C_1-C_6)$alkyl- of $R^4$ is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

8. The compound of claim 1, wherein $R^4$ is phenyl($C_1$-$C_3$)alkyl- wherein any phenyl($C_1$-$C_3$)alkyl- of $R^4$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy.

9. The compound of claim 1, wherein $R^5$ is hydrogen, aryl or aryl($C_1$-$C_6$)alkyl- wherein any aryl or aryl($C_1$-$C_6$)alkyl- of $R^5$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy, provided that when $R^5$ is hydrogen and $R^4$ is optionally substituted phenyl, then n is not 0 or 1.

10. The compound of claim 1, wherein $R^5$ is hydrogen, phenyl or phenyl($C_1$-$C_6$) alkyl- wherein any phenyl or phenyl($C_1$-$C_6$)alkyl- of $R^5$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy provided that when $R^5$ is hydrogen and $R^4$ is optionally substituted phenyl, then n is not 0 or 1.

11. The compound of claim 1, wherein $R^5$ is aryl or aryl($C_1$-$C_6$)alkyl- wherein any aryl or aryl($C_1$-$C_6$)alkyl- of $R^5$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy.

12. The compound of claim 1, wherein $R^5$ is phenyl or phenyl($C_1$-$C_6$)alkyl- wherein any phenyl or phenyl($C_1$-$C_6$) alkyl- of $R^5$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy.

13. The compound of claim 1, wherein $R^5$ is phenyl($C_1$-$C_2$)alkyl- wherein any phenyl($C_1$-$C_2$)alkyl- of $R^5$ is optionally substituted with one or more groups independently selected from halo, ($C_1$-$C_4$)alkyl, ($C_1$-$C_4$)haloalkyl, ($C_1$-$C_4$)alkoxy and ($C_1$-$C_4$)haloalkoxy.

14. The compound of claim 1, wherein $R^1$ is ($C_3$-$C_{12}$) alkyl substituted with two groups independently selected from —$NR^{b1}R^{c1}$.

15. The compound of claim 1, wherein $R^1$ is

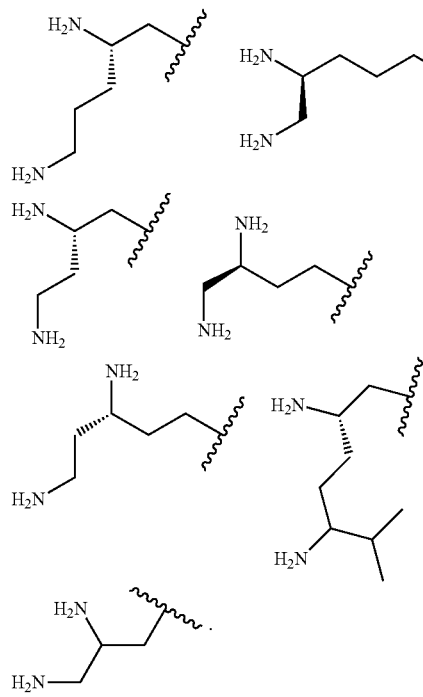

or

16. The compound of claim 1 which is:

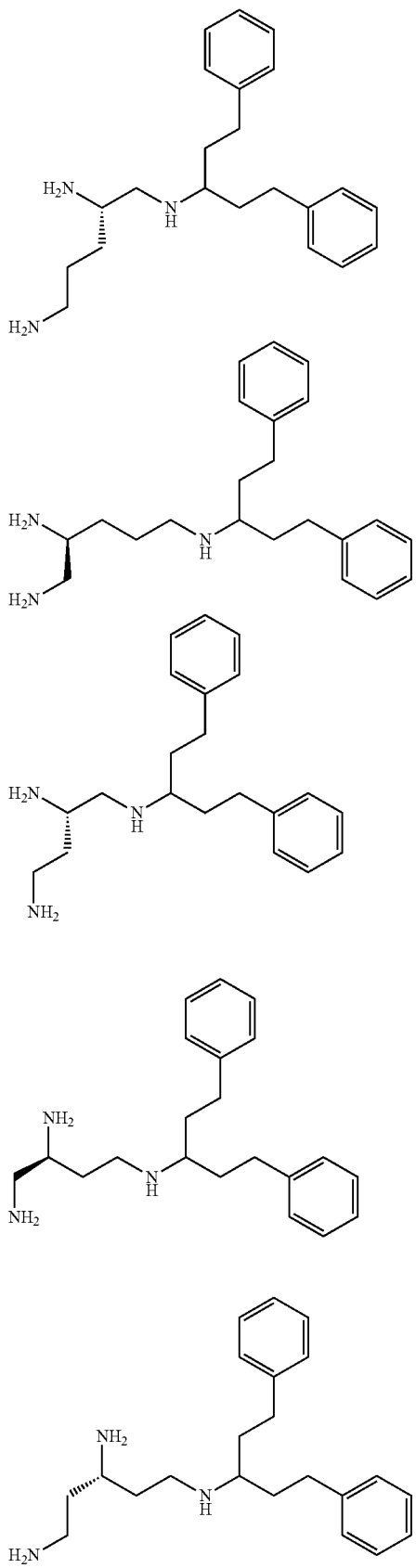

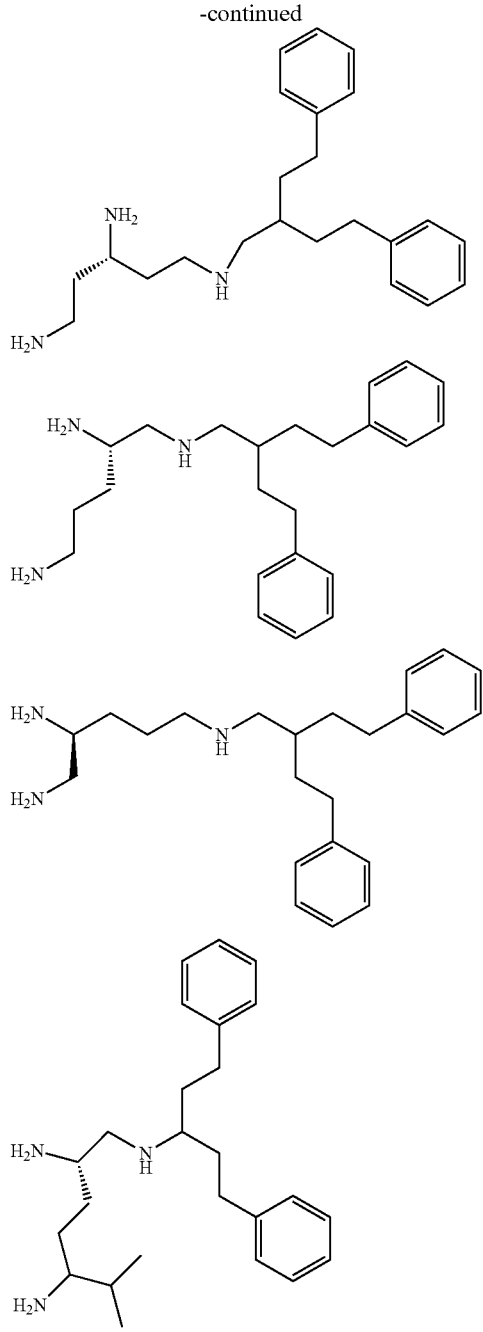

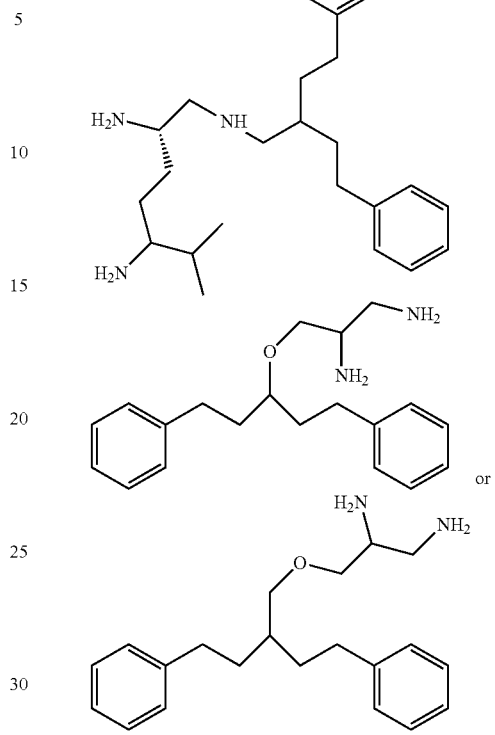

or a salt thereof.

17. A pharmaceutical composition comprising a compound of formula I as described in claim 1 or a pharmaceutically acceptable salt thereof, and a pharmaceutically acceptable vehicle.

18. A pharmaceutical composition comprising a compound of formula I as described in claim 1 or a pharmaceutically acceptable salt thereof, one or more antibacterial agents and a pharmaceutically acceptable vehicle.

19. A method of inhibiting a bacterial efflux pump in an animal comprising administering to the animal a compound of formula I as described in claim 1 or a pharmaceutically acceptable salt thereof.

20. A method of treating a bacterial infection in an animal comprising co-administering to the animal a compound of formula I as described in claim 1 or a pharmaceutically acceptable salt thereof and one or more antibacterial agents.

* * * * *